(12) United States Patent
Higashitsutsumi et al.

(10) Patent No.: US 10,078,254 B2
(45) Date of Patent: Sep. 18, 2018

(54) IMAGING DEVICE AND IMAGING METHOD

(71) Applicant: Sony Corporation, Tokyo (JP)

(72) Inventors: Yoshihito Higashitsutsumi, Kanagawa (JP); Shinichiro Gomi, Tokyo (JP); Jun Iwama, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/123,760

(22) PCT Filed: Apr. 3, 2015

(86) PCT No.: PCT/JP2015/060648
§ 371 (c)(1),
(2) Date: Sep. 6, 2016

(87) PCT Pub. No.: WO2015/174163
PCT Pub. Date: Nov. 19, 2015

(65) Prior Publication Data
US 2017/0052430 A1    Feb. 23, 2017

(30) Foreign Application Priority Data

May 14, 2014 (JP) .................. 2014-100552

(51) Int. Cl.
*G03B 15/06* (2006.01)
*G02F 1/335* (2006.01)
(Continued)

(52) U.S. Cl.
CPC ............... *G03B 15/06* (2013.01); *A61B 5/00* (2013.01); *A61B 5/0022* (2013.01);
(Continued)

(58) Field of Classification Search
None
See application file for complete search history.

(56) References Cited

U.S. PATENT DOCUMENTS

| 3,762,298 A | * | 10/1973 | Johnson | ................... G03B 3/02 396/65 |
| 4,988,158 A | * | 1/1991 | Yamamoto | ............ G02B 21/12 349/1 |

(Continued)

FOREIGN PATENT DOCUMENTS

| JP | 03-135276 A | 6/1991 |
| JP | 11-308496 A | 11/1999 |

(Continued)

OTHER PUBLICATIONS

U.S. Appl. No. 13/953,809, filed Jul. 30, 2013, Sekiguchi et al.
(Continued)

*Primary Examiner* — William B Perkey
(74) *Attorney, Agent, or Firm* — Wolf, Greenfield & Sacks, P.C.

(57) ABSTRACT

An imaging device includes a camera 31, a light source 32, a polarizer 35 arranged between the camera 31 plus the light source 32 and an object 11, and a spatial light modulator 40A arranged between the polarizer 35 and the object 11 to control a revolution angle of an emitting light polarization plane relative to an incident light polarization plane.

13 Claims, 11 Drawing Sheets

(51) Int. Cl.
 *G01N 21/21* (2006.01)
 *G02B 5/30* (2006.01)
 *H04N 5/225* (2006.01)
 *G01B 11/30* (2006.01)
 *A61B 5/00* (2006.01)
 *G03B 15/03* (2006.01)
 *G02F 1/1335* (2006.01)
 *G03B 15/05* (2006.01)
 *G03B 15/14* (2006.01)
 *A61B 5/107* (2006.01)
 *G02B 21/06* (2006.01)

(52) U.S. Cl.
 CPC ............ *A61B 5/0077* (2013.01); *A61B 5/442* (2013.01); *G01B 11/303* (2013.01); *G01N 21/21* (2013.01); *G02B 5/3083* (2013.01); *G02F 1/133528* (2013.01); *G03B 15/03* (2013.01); *G03B 15/05* (2013.01); *G03B 15/14* (2013.01); *H04N 5/225* (2013.01); *H04N 5/2256* (2013.01); *A61B 5/107* (2013.01); *G01N 2201/0675* (2013.01); *G02B 21/06* (2013.01)

(56) References Cited

U.S. PATENT DOCUMENTS

| | | | | |
|---|---|---|---|---|
| 5,384,616 A * | 1/1995 | Wilson | ............... | G03B 7/16 315/157 |
| 6,088,541 A * | 7/2000 | Meyer | ............... | G03B 15/05 396/155 |
| 6,118,476 A * | 9/2000 | Morito | ............... | G02B 21/361 348/65 |
| 6,430,371 B1 * | 8/2002 | Cho | ............... | G03B 15/03 396/14 |
| 7,729,607 B2 * | 6/2010 | Karim | ............... | G03B 15/03 348/342 |
| 8,867,324 B2 | 10/2014 | Sekiguchi et al. | | |
| 9,268,197 B1 * | 2/2016 | DiGregorio | ............... | G03B 9/70 |
| 9,417,173 B2 | 8/2016 | Nitta | | |
| 2002/0087085 A1 * | 7/2002 | Dauga | ............... | A61B 5/0059 600/476 |
| 2010/0245823 A1 * | 9/2010 | Chhibber | ............... | A61B 5/0059 356/366 |
| 2013/0148326 A1 * | 6/2013 | Goldfain | ............... | G01J 3/0224 362/19 |
| 2014/0036651 A1 | 2/2014 | Sekiguchi et al. | | |
| 2015/0177113 A1 | 6/2015 | Nitta | | |
| 2016/0003610 A1 * | 1/2016 | Lampert | ............... | G01B 11/24 356/4.01 |
| 2017/0065178 A1 | 3/2017 | Suzuki et al. | | |
| 2017/0156605 A1 | 6/2017 | Nakao et al. | | |

FOREIGN PATENT DOCUMENTS

JP   2007-264410 A   10/2007
JP   2008-017396 A   1/2008

OTHER PUBLICATIONS

U.S. Appl. No. 14/418,711, filed Jan. 30, 2015, Nitta.
U.S. Appl. No. 15/123,285, filed Sep. 2, 2016, Suzuki et al.
U.S. Appl. No. 15/313,573, filed Nov. 23, 2016, Nakao et al.
U.S. Appl. No. 15/325,558, filed Jan. 11, 2017, Nakao et al.

* cited by examiner

OPTIMUM ARRANGEMENT ANGLE = Ψ

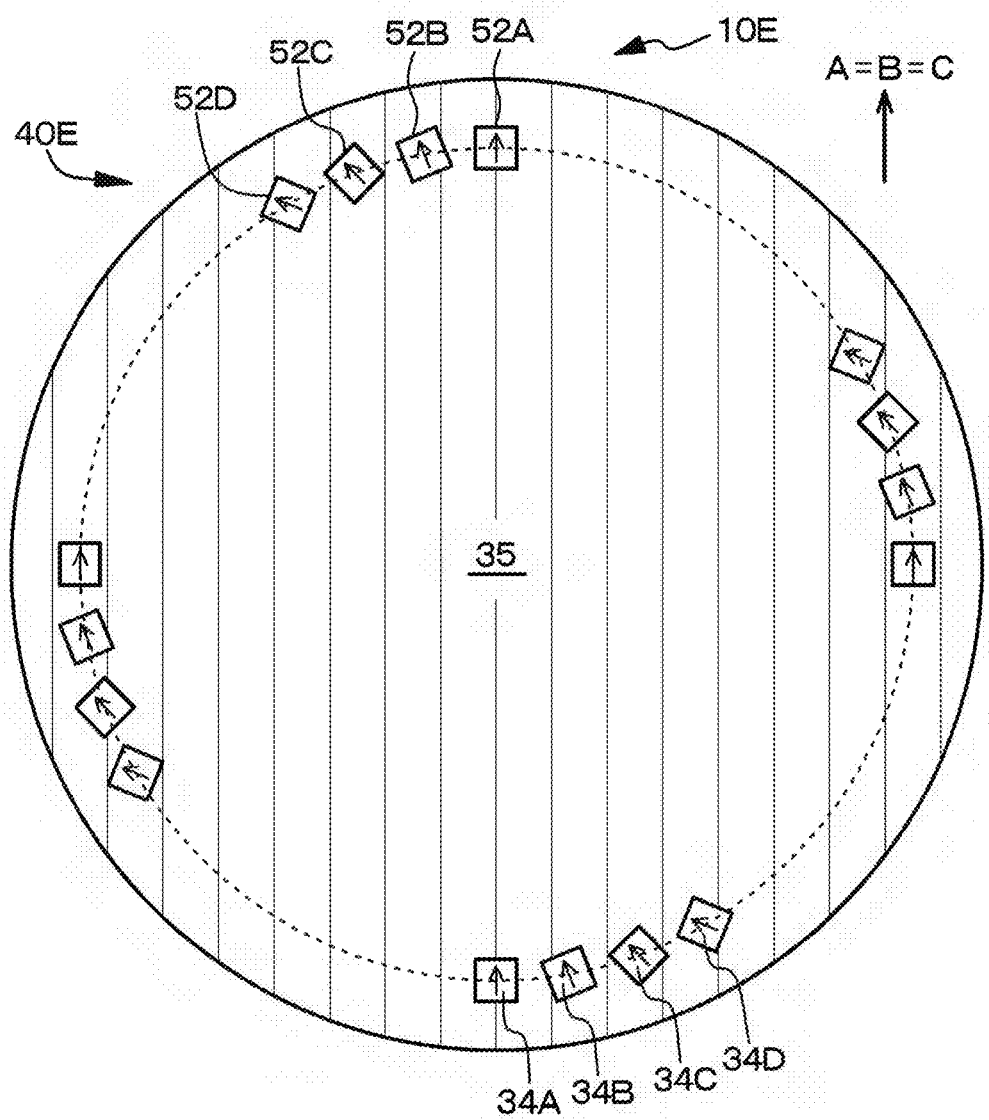

IMAGING DEVICE AND IMAGING METHOD

CROSS-REFERENCE TO RELATED APPLICATIONS

This application is a National Stage of International Application No. PCT/JP2015/060648, filed in the Japanese Patent Office as a Receiving office on Apr. 3, 2015, which claims priority to Japanese Patent Application Number 2014-100552, filed in the Japanese Patent Office on May 14, 2014, each of which is hereby incorporated by reference in its entirety.

TECHNICAL FIELD

The present disclosure relates to an imaging device and an imaging method.

BACKGROUND ART

When an imaging device for observing epidermis (skin), scalp, and the like is used to capture an image on the basis of reflected light reflected on a surface of the epidermis, a surface state of the epidermis such as skin roughness and texture of skin can be observed. Meanwhile, when an image is captured on the basis of scattered light scattered at the inside of the epidermis, an inner state of the skin such as a spot and dullness can be observed. Such an imaging device is publicly known through Japanese Patent Application Laid-Open No. 11-308496, for example. This imaging device is provided with two polarized illumination systems configured to selectively irradiate an object to be observed with respective rays of polarized light whose vibration directions intersect with each other orthogonally or substantially orthogonally, while an analyzer having a vibration direction matching or substantially parallel to the vibration direction of the polarized light from one polarized illumination system and at the same time intersecting with the vibration direction of the polarized light from another polarized illumination system orthogonally or substantially orthogonally is disposed therein on an optical path extending from the object to be observed to a CCD element configured to image the object to be observed.

CITATION LIST

Patent Document

Patent Document 1: Japanese Patent Application Laid-Open No. 11-308496

SUMMARY OF THE INVENTION

Problems to be Solved by the Invention

However, two polarized illumination systems are necessary in this imaging device disclosed in the laid-open patent publication and the structure thereof is thus complicated. In addition, it is required to optimize (change), in accordance with an object (object to be observed), a polarization state of light with which the object is irradiated. However, it is difficult for this imaging device disclosed in the laid-open patent publication to respond to such a requirement.

Therefore, an object of the present disclosure is to provide an imaging device and an imaging method using this imaging device, which have simple configurations and structures and also are capable of optimizing (capable of changing), in accordance with an object, a polarization state of light with which the object is irradiated.

Solutions to Problems

An imaging device according to a first mode of the present disclosure for achieving the aforementioned object includes:
a camera;
a light source;
a polarizer arranged between the camera plus the light source and an object; and
a spatial light modulator arranged between the polarizer and the object to control a revolution angle of an emitting light polarization plane relative to an incident light polarization plane.

An imaging device according to a second mode of the disclosure for achieving the aforementioned object includes:
a camera;
a light source; and
a polarizer arranged between the camera plus the light source and an object, in which the polarizer is arranged rotatably with respect to the camera and the light source.

An imaging method according to the first mode of the disclosure for achieving the aforementioned object is an imaging method using an imaging device including:
a camera;
a light source;
a polarizer arranged between the camera plus the light source and an object; and
a spatial light modulator arranged between the polarizer and the object to control a revolution angle of an emitting light polarization plane relative to an incident light polarization plane, in which
the object is imaged with the camera while the revolution angle is changed.

An imaging method according to the second mode of the disclosure for achieving the aforementioned object is an imaging method using an imaging device including:
a camera;
a light source constituted by a plurality of light emitting units arranged apart from one another;
a polarizer arranged between the camera plus the light source and an object; and
a ½-wave plate arranged between the polarizer and the object to transmit light emitting from each of at least some of the plurality of light emitting units, in which
the object is imaged with the camera while the ½-wave plate and the polarizer are arranged such that a value of an angle $\phi$ formed by an optical axis of the ½-wave plate and a transmission axis of the polarizer is set to a value other than zero degrees.

Effects of the Invention

An imaging device according to a first mode of the present disclosure is provided with a polarizer arranged between a camera plus a light source and an object, and a spatial light modulator arranged between the polarizer and the object to control a revolution angle of an emitting light polarization plane relative to an incident light polarization plane. As a result, although a configuration and a structure thereof are simple, a polarization state of light with which the object is irradiated can be optimized in accordance with the object. Additionally, in an imaging device according to a second mode of the disclosure, a polarizer arranged rotatably with respect to a camera and a light source is provided between the camera plus the light source and an object. As a result, although a configuration and a structure thereof are simple, a polarization state of light from the light source can be optimized in accordance with the object. Furthermore, in an imaging method according to the first mode of the disclosure, the object is imaged with the camera while a revolution angle of the emitting light polarization plane at the spatial light modulator relative to the incident light polarization plane is changed. Meanwhile, in an imaging method according to the second mode of the disclosure, the object is imaged with the camera while a ½-wave plate and the polarizer are arranged such that a value of an angle φ formed by an optical axis of the ½-wave plate and a transmission axis of the polarizer is set to a value other than zero degrees. Therefore, a polarization state of light with which the object is irradiated can be optimized in accordance with the object. Note that the effects described in the present description merely serve as examples and not construed to be limited. There may be an additional effect as well.

BRIEF DESCRIPTION OF DRAWINGS

FIG. 1A is a conceptual diagram of an imaging device according to a first embodiment, whereas

FIG. 5A is a conceptual diagram of an imaging device according to a third embodiment through a seventh embodiment, whereas

FIG. 8 is a conceptual diagram illustrating an arrangement state of a polarizer and a spatial light modulator (½-wave plate) in the imaging device according to the fifth embodiment.

MODE FOR CARRYING OUT THE INVENTION

Figure 1A:
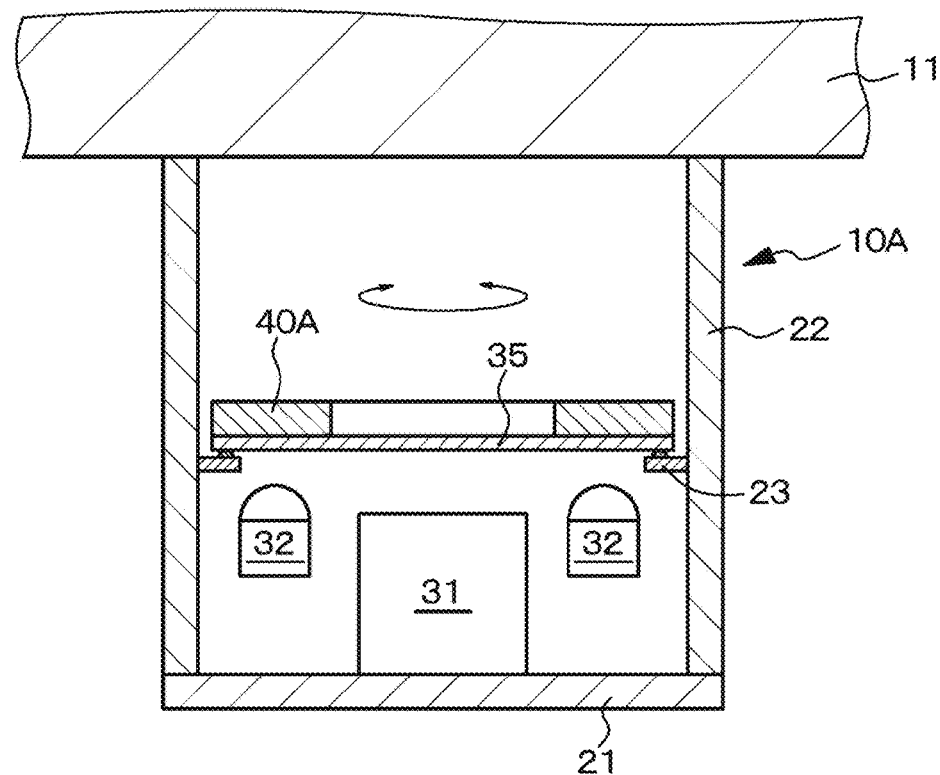

Hereinafter, the present disclosure will be described on the basis of embodiments with reference to the drawings. However, the disclosure is not limited to the embodiments and various numerical values and materials in the embodiments are examples. Note that the description will be given in the following order.

1. Description regarding imaging devices according to a first mode and a second mode of the disclosure, imaging methods according to the first mode and the second mode of the disclosure, and an overview 2. First embodiment (the imaging device according to the first mode of the disclosure, imaging devices according to a first A mode and a first A-1 mode of the disclosure, and an imaging method according to the first A mode of the disclosure)

3. Second embodiment (a modification of the first embodiment; an imaging device according to a first A-2 mode of the disclosure and an imaging method according to a first B mode of the disclosure)

4. Third embodiment (another modification of the first embodiment; an imaging device according to the first B mode of the disclosure, an imaging device according to a first B-1 mode of the disclosure, and the imaging method according to the second mode of the disclosure)

5. Fourth embodiment (a modification of the third embodiment; an imaging device according to a first B-2 mode of the disclosure and an imaging method according to a second A mode of the disclosure)

6. Fifth embodiment (another modification of the third embodiment; an imaging device according to a first C mode of the disclosure, an imaging device according to a first C-1 mode of the disclosure, an imaging method according to a second B mode of the disclosure, and an imaging method according to a second B-1 mode of the disclosure)

7. Sixth embodiment (still another modification of the third embodiment; an imaging device according to a first C-2 mode of the disclosure and an imaging method according to a second B-2 mode of the disclosure)

8. Seventh embodiment (still another modification of the third embodiment; an imaging device according to a first C-3 mode of the disclosure and an imaging method according to a second C mode of the disclosure)

9. Eighth embodiment (the imaging device according to the second mode of the disclosure) and others

[Description Regarding Imaging Devices According to First Mode and Second Mode of Disclosure, Imaging Methods According to First Mode and Second Mode of Disclosure, and Overview]

In the imaging device according to the first mode of the disclosure, a form can be employed in which a spatial light modulator is formed by a device provided with a transmission-type liquid crystal layer. The imaging device having such a form is called an "imaging device according to the first A mode of the disclosure" for convenience.

In the imaging device according to the first A mode of the disclosure, a form can be employed in which light emitting from a light source and passing through a polarizer and the spatial light modulator to collide with an object reaches a camera after passing through the polarizer. The imaging device having such a form is called an "imaging device according to the first A-1 mode of the disclosure" for convenience. Additionally, in this case, a form can be employed in which the polarizer is arranged rotatably with respect to the camera and the light source; and the spatial light modulator is fixed with respect to the polarizer. Furthermore, a form can be employed in which a revolution angle is changed to, for example, 0 degrees, 45 degrees, 90 degrees, and 135 degrees.

Alternatively, in the imaging device according to the first A mode of the disclosure, a form can be employed in which the spatial light modulator is constituted by an annular-shaped first region and a second region positioned on an inner side of the first region; and light emitting from the light source and passing through the polarizer and the first region of the spatial light modulator to collide with the object reaches the camera after passing through the second region of the spatial light modulator and the polarizer. The imaging device having such a form is called an "imaging device according to the first A-2 mode of the disclosure" for convenience. Additionally, in this case, a form can be employed in which the polarizer and the spatial light modulator are fixed with respect to the camera and the light source. Furthermore, when a value of an angle formed by an incident light polarization plane at the first region of the spatial light modulator and an emitting light polarization plane at the second region of the spatial light modulator is assumed as $\psi$ (in degree) and a value of an angle formed by an emitting light polarization plane at the first region of the spatial light modulator and the emitting light polarization plane at the second region of the spatial light modulator is assumed as $\psi'$ (in degree), a form can be employed in which the revolution angle at the first region of the spatial light modulator is changed by controlling operation of the first region of the spatial light modulator such that $\psi'$ is set to $\psi$ and a value different from $\psi$, where $\psi'=\psi$, $\psi'=(\psi+45)$, $\psi'=(\psi+90)$, and $\psi'=(\psi+135)$ can be set and additionally, $\psi=0$ can be set.

Alternatively, in the imaging device according to the first mode of the disclosure, as described above, a form can be employed in which light emitting from the light source and passing through the polarizer and the spatial light modulator to collide with the object reaches the camera after passing through the polarizer. In the imaging device including such a form according to the first mode of the disclosure, a form can be employed in which the light source is constituted by a plurality of light emitting units arranged apart from one another, the spatial light modulator is formed by a ½-wave plate that transmits light emitting from each of some of the plurality of light emitting units, and a value of an angle $\phi$ formed by an optical axis of the ½-wave plate and the incident light polarization plane is set to a value other than zero degrees. The imaging device having such a form is called an "imaging device according to the first B mode of the disclosure" for convenience.

Additionally, in the imaging device according to the first B mode of the disclosure, a form can be employed in which the polarizer and the ½-wave plate are fixed with respect to the camera and the light source; and the value of the angle $\phi$ is 45 degrees. The imaging device having such a form is called an "imaging device according to the first B-1 mode of the disclosure" for convenience. Alternatively, in the imaging device according to the first B mode of the disclosure, a form can be employed in which the polarizer is arranged rotatably with respect to the camera and the light source; the ½-wave plate is fixed with respect to the polarizer; and the value of the angle $\phi$ is 45 degrees. The imaging device having such a form is called an "imaging device according to the first B-2 mode of the disclosure" for convenience. In the imaging device according to the first B-2 mode of the disclosure, a form can be employed in which the plurality of ½-wave plates is arranged in an annular shape; and the polarizer is arranged at a position at zero degrees, a position at 45 degrees, a position at 90 degrees, and a position at 135 degrees with respect to an optimum arrangement angle of the polarizer relative to the camera and the light source.

Alternatively, in the imaging device according to the first mode of the disclosure, as described above, a form can be employed in which light emitting from the light source and passing through the polarizer and the spatial light modulator to collide with the object reaches the camera after passing through the polarizer. In the imaging device including such a form according to the first mode of the disclosure, a form can be employed in which the light source is constituted by a plurality of light emitting units arranged apart from one another, the spatial light modulator is formed by M number of ½-wave plate groups, each of which is constituted by ½-wave plates that transmit light emitting from each of the plurality of light emitting units, and when a value of an angle formed by the incident light polarization plane and the optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_m$, $\phi_1=0$ (in degree)

$|\phi_m-\phi_{m-1}|=\phi_0$ are satisfied. The imaging device having such a form is called an "imaging device according to the first C mode of the disclosure" for convenience.

Additionally, in the imaging device according to the first C mode of the disclosure, a form can be employed in which the polarizer and the ½-wave plate are fixed with respect to the camera and the light source. The imaging device having such a form is called an "imaging device according to the first C-1 mode of the disclosure" for convenience. In addition, in this case, M=4 and $\phi_0=22.5$ degrees can be set.

Alternatively, in the imaging device according to the first C mode of the disclosure, a form can be employed in which the polarizer is arranged rotatably with respect to the camera and the light source; and the ½-wave plate is fixed with respect to the polarizer. The imaging device having such a form is called an "imaging device according to the first C-2 mode of the disclosure" for convenience. Additionally, in this case, a form can be employed in which the plurality of ½-wave plates is arranged in an annular shape; and the polarizer is arranged at a position at zero degrees and a position at 90 degrees with respect to the optimum arrangement angle of the polarizer relative to the camera and the light source, and furthermore, M=2 and $\phi_0=22.5$ degrees can be set.

Alternatively, in the imaging device according to the first C mode of the disclosure, a form can be employed in which the polarizer is arranged rotatably with respect to the camera and the light source; and the ½-wave plate is arranged rotatably with respect to the polarizer. The imaging device having such a form is called an "imaging device according to the first C-3 mode of the disclosure" for convenience. Additionally, in this case, a form can be employed in which the plurality of ½-wave plates is arranged in an annular shape; and the polarizer is arranged so as to be fixed at zero degrees with respect to the optimum arrangement angle of the polarizer relative to the camera and the light source while the ½-wave plate is arranged at a position at zero degrees and a position at 45 degrees with respect thereto, and furthermore, M=2 and $\phi_0$=22.5 degrees can be set.

In the imaging device according to the second mode of the disclosure, a form can be employed in which the polarizer is arranged at a position at zero degrees, a position at 45 degrees, a position at 90 degrees, and a position at 135 degrees with respect to the optimum arrangement angle of the polarizer relative to the camera and the light source. Additionally, the object is imaged while the polarizer is arranged at a position at zero degrees, a position at 45 degrees, a position at 90 degrees, and a position at 135 degrees.

In the imaging method according to the first mode of the disclosure, a form can be employed in which the object is imaged with the camera while the polarizer and the spatial light modulator are rotated with respect to the camera and the light source in a state where the revolution angle is fixed and then, the optimum arrangement angle of the polarizer relative to the camera and the light source is determined such that an optimum reflection characteristic of the object is obtained, and subsequently, the object is imaged with the camera while the revolution angle is changed in a state where the polarizer and the spatial light modulator are fixed at the optimum arrangement angle. The imaging method having such a form is called an "imaging method according to the first A mode of the disclosure" for convenience. Here, a form can be employed in which the spatial light modulator is formed by a device provided with a transmission-type liquid crystal layer and additionally, light emitting from a light source and passing through the polarizer and the spatial light modulator to collide with the object reaches the camera after passing through the polarizer. In this case, a form can be employed in which the object is imaged with the camera while the revolution angle is changed to zero degrees, 45 degrees, 90 degrees, and 135 degrees. Specifically, in the imaging method according to the first A mode of the disclosure, an image is captured using the imaging device according to the first A-1 mode of the disclosure, substantially.

Alternatively, in the imaging method according to the first mode of the disclosure, a form can be employed in which the object is imaged with the camera while the revolution angle is changed in a state where the polarizer and the spatial light modulator are fixed with respect to the camera and the light source and then, an optimum revolution angle relative to the camera and the light source is determined such that the optimum reflection characteristic of the object is obtained, and subsequently, the object is imaged with the camera while the revolution angle is set to the optimum revolution angle and a value different from the optimum revolution angle in a state where the polarizer and the spatial light modulator are fixed with respect to the camera and the light source. The imaging method having such a form is called an "imaging method according to the first B mode of the disclosure" for convenience. Here, a form can be employed in which the spatial light modulator is constituted by an annular-shaped first region and a second region positioned on an inner side of the first region; and light emitting from the light source and passing through the polarizer and the first region of the spatial light modulator to collide with the object reaches the camera after passing through the second region of the spatial light modulator and the polarizer. Additionally, when a value of an angle formed by the incident light polarization plane at the first region of the spatial light modulator and an emitting light polarization plane at the second region of the spatial light modulator is assumed as $\psi$ (in degree) and a value of an angle formed by an emitting light polarization plane at the first region of the spatial light modulator and the emitting light polarization plane at the second region of the spatial light modulator is assumed as $\psi'$ (in degree), a form can be employed in which the object is imaged with the camera while the revolution angle at the first region of the spatial light modulator is changed by controlling operation of the first region of the spatial light modulator such that $\psi'$ is set to $\psi$ and a value different from $\psi$. Additionally, in this case, a form can be employed in which $\psi'=\psi$, $\psi'=(\psi+45)$, $\psi'=(\psi+90)$, and $\psi'=(\psi+135)$ are set and furthermore, $\psi=0$ can be set. Specifically, in the imaging method according to the first B mode of the disclosure, an image is captured using the imaging device according to the first A-2 mode of the disclosure, substantially.

In the imaging method according to the second mode of the disclosure, a form can be employed in which the object is imaged with the camera while the polarizer and the ½-wave plate are rotated with respect to the camera and the light source and then, the optimum arrangement angle of the polarizer and the ½-wave plate relative to the camera and the light source is determined such that the optimum reflection characteristic of the object is obtained, and subsequently, the object is imaged with the camera while the polarizer and the ½-wave plate are rotated by using the optimum arrangement angle as a reference. The imaging method having such a form is called an "imaging method according to the second A mode of the disclosure" for convenience. Additionally, in this case, the value of the angle $\phi$ can be set to 45 degrees and furthermore, a form can be employed in which the plurality of ½-wave plates is arranged in an annular shape; and the object is imaged with the camera while the polarizer is arranged at a position at zero degrees, a position at 45 degrees, a position at 90 degrees, and a position at 135 degrees with respect to the optimum arrangement angle. Specifically, in the imaging method according to the second A mode of the disclosure, an image is captured using the imaging device according to the first B-2 mode of the disclosure, substantially.

Alternatively, in the imaging method according to the second mode of the disclosure, a form can be employed in which M number of ½-wave plate groups is provided, each of which is constituted by the plurality of ½-wave plates arranged apart from one another, the polarizer is arranged rotatably with respect to the camera and the light source, the ½-wave plate is fixed with respect to the polarizer, when a value of an angle formed by the incident light polarization plane and the optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_m$, $\phi_1=0$ (in degree)

$|\phi_m-\phi_{m-1}|=\phi_0$ are satisfied, and the object is imaged with the camera while the polarizer is rotated with respect to the camera and the light source and, after the optimum arrangement angle of the polarizer relative to the camera and the light source is determined such that the optimum reflection characteristic of the object is obtained, the object is imaged with the camera. The imaging method having such a form is called an "imaging method according to the second B mode of the disclosure" for convenience. Specifically, in the imaging method according to the second B mode of the disclosure, an image is captured using the imaging device according to the first C mode of the disclosure, substantially.

In the imaging method according to the second B mode of the disclosure, a form can be employed in which the object is imaged with the camera while the polarizer is arranged at the optimum arrangement angle. The imaging method having such a form is called an "imaging method according to the second B-1 mode of the disclosure" for convenience. In addition, in this case, M=4 and $\phi_0$=22.5 degrees can be set. Specifically, in the imaging method according to the second B-1 mode of the disclosure, an image is captured using the imaging device according to the first C-1 mode of the disclosure, substantially.

Alternatively, in the imaging method according to the second B mode of the disclosure, a form can be employed in which the plurality of ½-wave plates is arranged in an annular shape; and the object is imaged with the camera while the polarizer is arranged at a position at zero degrees and a position at 90 degrees with respect to the optimum arrangement angle. The imaging method having such a form is called an "imaging method according to the second B-2 mode of the disclosure" for convenience. Additionally, in this case, M=2 and $\phi_0$=22.5 degrees can be set. Specifically, in the imaging method according to the second B-2 mode of the disclosure, an image is captured using the imaging device according to the first C-2 mode of the disclosure, substantially.

Alternatively, in the imaging method according to the second mode of the disclosure, a form can be employed in which M number of ½-wave plate groups is provided, each of which is constituted by the plurality of ½-wave plates arranged apart from one another, the polarizer is arranged rotatably with respect to the camera and the light source, the entire ½-wave plates are arranged rotatably with respect to the polarizer, when a value of an angle formed by the incident light polarization plane and the optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_m$, $\phi_1=0$ (in degree)

$|\phi_m-\phi_{m-1}|=\phi_0$ are satisfied, the object is imaged with the camera while the polarizer and the entire ½-wave plates are rotated with respect to the camera and the light source and then, the optimum arrangement angle of the polarizer relative to the camera and the light source is determined such that the optimum reflection characteristic of the object is obtained, and subsequently, the object is imaged with the camera while the entire ½-wave plates are rotated in a state where the polarizer is fixed at the optimum arrangement angle. The imaging method having such a form is called an "imaging method according to the second C mode of the disclosure" for convenience. Additionally, in this case, a form can be employed in which the entire ½-wave plates are arranged in an annular shape; and the object is imaged with the camera while the entire ½-wave plates are arranged at a position at zero degrees and a position at 45 degrees with respect to the optimum arrangement angle and furthermore, M=2 and $\phi_0$=22.5 degrees can be set. Specifically, in the imaging method according to the second C mode of the disclosure, an image is captured using the imaging device according to the first C-3 mode of the disclosure, substantially.

In the imaging methods according to the disclosure, prior to imaging the object, a sort of calibration regarding the arrangement angles and the revolution angles of the polarizer and the spatial light modulator relative to the camera and the light source is carried out. Specific details are as follows.

(A) The object is imaged with the camera while the polarizer and the spatial light modulator are rotated with respect to the camera and the light source in a state where the revolution angle is fixed and then, the optimum arrangement angle of the polarizer relative to the camera and the light source is determined such that the optimum reflection characteristic of the object is obtained (the imaging method according to the first A mode of the disclosure). Alternatively, (B) The object is imaged with the camera while the revolution angle is changed in a state where the polarizer and the spatial light modulator are fixed with respect to the camera and the light source and then, the optimum revolution angle relative to the camera and the light source is determined such that the optimum reflection characteristic of the object is obtained (the imaging method according to the first B mode of the disclosure). Alternatively, (C) The object is imaged with the camera while the polarizer and the ½-wave plate are rotated with respect to the camera and the light source and then, the optimum arrangement angle of the polarizer and the ½-wave plate relative to the camera and the light source is determined such that the optimum reflection characteristic of the object is obtained (the imaging method according to the second A mode of the disclosure). Alternatively, (D) The object is imaged with the camera while the polarizer is rotated with respect to the camera and the light source and then, the optimum arrangement angle of the polarizer relative to the camera and the light source is determined such that the optimum reflection characteristic of the object is obtained (the imaging method according to the second B mode of the disclosure). Alternatively, (E) The object is imaged with the camera while the polarizer and the entire ½-wave plates are rotated with respect to the camera and the light source and then, the optimum arrangement angle of the polarizer relative to the camera and the light source is determined such that the optimum reflection characteristic of the object is obtained (the imaging method according to the second C mode of the disclosure).

Here, the "optimum arrangement angle" represents an arrangement angle at which an image with highest contrast (for example, an image obtained through reflected light reflected on a surface of the object) can be obtained when the object is imaged with the camera. The "optimum arrangement angle" in the imaging device according to the disclosure is similar to this.

In the imaging device according to the first A mode of the disclosure, a device provided with a transmission-type liquid crystal layer (hereinafter, called a "liquid crystal device" in some cases for convenience) can be configured as a device obtained by excluding the polarizers on a light source side and an object side from a usual liquid crystal display device. Specifically, the liquid crystal device is constituted by at least a first substrate, a second electrode, a liquid crystal layer, a first electrode, and a second electrode. The liquid crystal layer is disposed between the first substrate and a second substrate, while the first electrode is formed on a plane of the first substrate opposing the second substrate and the second electrode is formed on a plane of the second substrate opposing the first substrate. Accordingly, as a result of a change in an array of liquid crystal molecules in the liquid crystal layer caused depending on a voltage applied between the first electrode and the second electrode, the revolution angle of the emitting light polarization plane of emitting light relative to the incident light polarization plane of incident light can be controlled. A polarization plane of light emitting from the light source and passing through the polarizer matches the incident light polarization plane of incident light entering the liquid crystal device. Note that the polarizer on the light source side in the usual liquid crystal display device may be used as the polarizer constituting the imaging device.

The polarizer is used to create linearly polarized light from natural light (nonpolarized) or circularly polarized light, where light passing through the polarizer is turned into the linearly polarized light vibrating in a direction of a transmission axis of the polarizer. Therefore, the polarization state of light emitting from the light source and passing through the polarizer to enter the spatial light modulator is the linearly polarized light. Besides, the polarization state of light emitting from the spatial light modulator is also the linearly polarized light. An absorption type polarizer (e.g., a polarizer produced from a plastic film) and a wire grid type polarizer can be exemplified as the polarizer. The polarization plane refers to a plane including a traveling direction of an electromagnetic wave and a magnetic field direction of the electromagnetic wave. Usually, the polarization state of reflected light reflected on the surface of the object, which is light having collided with the object, is approximately the linearly polarized light. Meanwhile, the polarization state of scattered light scattered at the inside of the object and outgoing from the object, which is light having collided with the object, is, for example, elliptically polarized light.

A wave plate is used to generate a phase difference between polarization components orthogonally intersecting with each other and the ½-wave plate (half-wave plate) generates a phase difference of π (180 degrees) to change a polarization direction of the linearly polarized light. The ½-wave plate can be produced from, for example, a plastic film. The optical axis (principal plane) of the ½-wave plate represents a fast axis or a slow axis in the ½-wave plate. The polarization plane of the linearly polarized light incident at an azimuth of φ (in degree) with respect to the optical axis of the ½-wave plate is caused to rotate by 2φ (in degree). Specifically, the revolution angle of the emitting light polarization plane of emitting light relative to the incident light polarization plane of incident light is 2φ (in degree).

The camera is simply obtained by a digital camera having generally known configuration and structure and any type of a camera can be used as long as the camera is of a type capable of obtaining a still image (including a video depending on cases). In addition, a type can be employed as well in which an imaging unit provided with a CCD element or a CMOS sensor to capture an image is separated from a control device that carries out various types of data processing and the imaging unit is arranged rotatably. The light source in the imaging device according to the first A mode of the disclosure can be configured as a plane light source device that illuminates an entire surface of the spatial light modulator, or alternatively, can be configured as a plurality of illumination means that illuminates a desired region of the spatial light modulator. Here, a light emitting element (e.g., a light emitting diode (LED)) can be exemplified as the illumination means, or alternatively, a combination of a light emitting device and a glass fiber can be exemplified as well. In the imaging device according to the first B mode of the disclosure, the light source is constituted by the plurality of light emitting units arranged apart from one another. As the light emitting unit, a light emitting element (e.g., a light emitting diode (LED)) can be exemplified, or alternatively, a combination of a light emitting device and a glass fiber can be exemplified as well. In order to prevent light from outside from entering the camera, it is preferable that a light blocking member having, for example, a cylindrical shape be arranged at a tip portion of the imaging device. With this, a tip of the light blocking member is simply made contact with the object while an image is captured. The light source in the imaging device according to the second mode of the disclosure can be made similar to the light source in the imaging device according to the first A mode or the first B mode of the disclosure.

When the imaging device according to the disclosure is used to capture an image on the basis of, for example, reflected light reflected on a surface of epidermis (skin), a surface state of the epidermis such as skin roughness and texture of skin can be observed. Meanwhile, when an image is captured on the basis of scattered light scattered at the inside of the epidermis (skin), an inner state of the skin such as a spot and dullness can be observed. Alternatively, when the imaging device according to the disclosure is used to, for example, suppress reflection on a surface of scalp, a blood flow in a capillary vessel under the scalp can be also observed.

Hereinafter, the imaging device and the imaging method according to the disclosure will be described on the basis of the embodiments. Terms to be used in the following description are defined as follows.

θ: a revolution angle of the emitting light polarization plane at the spatial light modulator (½-wave plate) relative to the incident light polarization plane at the spatial light modulator (½-wave plate)

φ: an angle formed by the optical axis of the ½-wave plate and the transmission axis of the polarizer $\xi_{in}$: an angle formed by the transmission axis of the polarizer and the incident light polarization plane at the spatial light modulator (½-wave plate)

$\xi_{out}$: an angle formed by the transmission axis of the polarizer and the emitting light polarization plane at the spatial light modulator (½-wave plate)

$\zeta_{in}$: an angle of the incident light polarization plane at the spatial light modulator (½-wave plate) when the optimum arrangement angle is used as a reference $\zeta_{out}$: an angle of the emitting light polarization plane at the spatial light modulator (½-wave plate) when the optimum arrangement angle is used as a reference ψ: an angle formed by the incident light polarization plane at the first region of the spatial light modulator and the emitting light polarization plane at the second region of the spatial light modulator ψ': an angle formed by the emitting light polarization plane at the first region of the spatial light modulator and the emitting light polarization plane at the second region of the spatial light modulator Additionally, various arrows in the drawings are defined as follows.

Arrow "A": a direction of an optimum arrangement

Arrow "B": the transmission axis of the polarizer (a polarization plane of light that has passed through the polarizer)

Arrow "C": the incident light polarization plane at the spatial light modulator (½-wave plate)

Arrow "D": the optical axis of the ½-wave plate

Arrow "E": the emitting light polarization plane at the spatial light modulator (½-wave plate)

Arrow "F": the emitting light polarization plane at the second region of the spatial light modulator Furthermore, the following definition is obtained.

θ: an angle formed by the arrow "C" and the arrow "E"
φ: an angle formed by the arrow "B" and the arrow "D"
$\xi_{in}$: an angle formed by the arrow "B" and the arrow "C"
$\xi_{out}$: an angle formed by the arrow "B" and the arrow "E"
$\zeta_{in}$: an angle formed by the arrow "A" and the arrow "C"
$\zeta_{out}$: an angle formed by the arrow "A" and the arrow "E"
ψ: an angle formed by the arrow "C" and the arrow "F"
ψ': an angle formed by the arrow "E" and the arrow "F"

First Embodiment

Figure 1B:
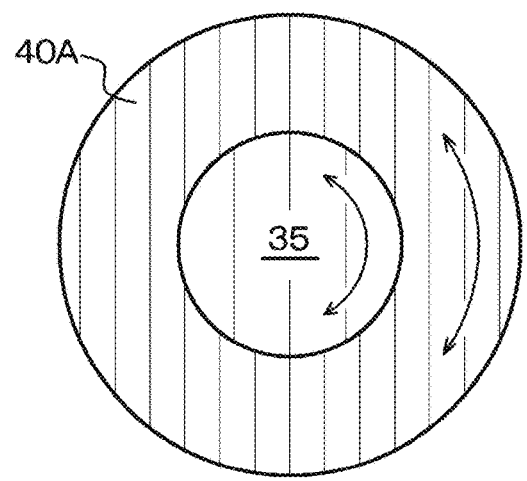
FIG. 1B is a conceptual diagram illustrating an arrangement state of a polarizer and a spatial light modulator.

The first embodiment relates to the imaging device according to the first mode of the disclosure, specifically, the imaging device according to the first A mode of the disclosure, more specifically, the imaging device according to the first A-1 mode of the disclosure. Meanwhile, the first embodiment relates to the imaging method according to the first mode of the disclosure, specifically, the imaging method according to the first A mode of the disclosure. A conceptual diagram of the imaging device according to the first embodiment is illustrated in FIG. 1A, whereas a conceptual diagram of an arrangement state of the polarizer and the spatial light modulator is illustrated in FIG. 1B. In addition, a conceptual diagram of an arrangement state of the polarizer and the spatial light modulator when the spatial light modulator is rotated in the imaging device according to the first embodiment is illustrated in each of FIG. 2A, FIG. 2B, FIG. 2C, and FIG. 2D.

The imaging device 10A, 10B, 10C, 10D, 10E, 10F, or 10G according to the first embodiment or the second embodiment through the seventh embodiment described later includes a camera 31,
a light source 32 or 33,
a polarizer 35 arranged between the camera 31 plus the light source 32 or 33 and an object 11, and
a spatial light modulator 40A, 40B, 40C, 40D, 40E, 40F, or 40G arranged between the polarizer 35 and the object 11. Here, each of the spatial light modulators 40A, 40B, 40C, 40D, 40E, 40F, and 40G controls a revolution angle θ of the emitting light polarization plane at each of the spatial light modulators 40A, 40B, 40C, 40D, 40E, 40F, and 40G relative to the incident light polarization plane at each of the spatial light modulators 40A, 401B, 40C, 40D, 40E, 40F, and 40G.

In the first embodiment or the second embodiment through the eighth embodiment described later, the camera 31 is simply obtained by a camera having generally known configuration and structure. The camera 31 is used to capture a still image (including a video depending on cases). The camera 31 is attached to a pedestal 21 of the imaging device. A light blocking member 22 having, for example, a cylindrical shape is arranged at a tip portion of the imaging device such that light from outside does not enter the camera 31. Specifically, the light blocking member 22 is attached to the pedestal 21. Image data obtained through imaging by the camera 31 is sent to a control device (not illustrated) provided in the camera 31 and then subjected to various types of data processing. Alternatively, the image data is sent to a computer group or the like constituting a system that assumes connection to a computer such as a personal computer and a server and a network such as cloud computing and then subjected to various types of data processing. Thereafter, an image obtained by carrying out various types of data processing is displayed on, for example, a monitor (not illustrated).

In the imaging device 10A or 10B according to the first embodiment or the second embodiment described later, the light source 32 is constituted by a plane light source device that illuminates an entire surface of the spatial light modulator 40A or 40B. In addition, each of the spatial light modulators 40A and 40B is formed by a device provided with a transmission-type liquid crystal layer (liquid crystal device). Specifically, this liquid crystal device is a device obtained by excluding the polarizers on alight source side and an object side from a usual liquid crystal display device. In other words, the liquid crystal device is fundamentally constituted by the first substrate, the second substrate, the liquid crystal layer, the first electrode, and the second electrode. The liquid crystal layer is disposed between the first substrate and the second substrate, while the first electrode is formed on a plane of the first substrate opposing the second substrate and the second electrode is formed on a plane of the second substrate opposing the first substrate. Accordingly, as a result of a change in an array of liquid crystal molecules in the liquid crystal layer caused depending on a voltage applied between the first electrode and the second electrode, the revolution angle θ of the emitting light polarization plane of emitting light relative to the incident light polarization plane of incident light can be controlled. Note that, unlike the usual liquid crystal display device, the array of liquid crystal molecules in the liquid crystal layer can be controlled in the liquid crystal device as a whole. Specifically, it is not necessary to control the array of liquid crystal molecules in the liquid crystal layer for each of pixels as in the usual liquid crystal display device.

Furthermore, the imaging device 10A according to the first embodiment is the imaging device according to the first A-1 mode of the disclosure and accordingly, light emitting from the light source 32 and passing through the polarizer 35 and the spatial light modulator 40A to collide with the object 11 (reflected light on the surface of the object 11 and scattered light scattered at the inside of the object 11) reaches the camera 31 after passing through the polarizer 35. In addition, the polarizer 35 is arranged rotatably with respect to the camera 31 and the light source 32. Meanwhile, the spatial light modulator 40A is fixed with respect to the polarizer 35.

Specifically, an assembly in which the spatial light modulator and the polarizer 35 are integrally assembled is arranged so as to be freely rotated on a ball bearing attached to a supporting unit 23 disposed so as to be set on an inner surface of the light blocking member 22. A motion of the assembly is regulated by a guide (not illustrated). Additionally, the assembly is rotated by a motor (not illustrated) and, for example, a combination of a rack gear and a pinion gear or various types of actuators so as to be stopped, paused, and fixed at a desired position. Note that, in this case, control can be carried out on the basis of an angle control signal generated at the control device and, for example, a rotary encoder. In this state, operation of the motor, illumination to the object by the light source, and imaging of the object by the camera are simply synchronized as appropriate. Alternatively, the assembly may be rotated manually. In this case, when a notch is provided, the assembly can be fixed at (rotated to) a position at a desired angle. In this state, illumination to the object by the light source and imaging of the object by the camera are simply synchronized as appropriate. The imaging devices according to the embodiments described below can be also configured fundamentally in a similar manner and thus, the assembly in which the spatial light modulator and the polarizer 35 are integrally assembled or the spatial light modulator can be arranged so as to be freely rotated.

The imaging method according to the first embodiment or the second embodiment described later is an imaging method using the imaging device according to the first embodiment or the second embodiment. In addition, the object 11 is imaged with the camera 31 while the revolution angle $\theta$ is changed.

It is generally considered that, when the amount of incident light on epidermis (skin) is assumed as "1", the light amount of reflected light on a surface of the epidermis is 0.05, the light amount of scattered light scattered at the inside thereof and then emitting to the outside is 0.55, and the remaining light amount of 0.40 is absorbed at the inside of the epidermis. Additionally, the polarization state of reflected light when light serving as the linearly polarized light is reflected on the surface of the epidermis is approximately the linearly polarized light, whereas the polarization state of scattered light scattered at the inside of the epidermis and then emitting from the epidermis is, for example, the elliptically polarized light. When the imaging device according to the first embodiment or the second embodiment through the eighth embodiment described later is used to image, for example, the epidermis (skin) such that a state of the epidermis is measured, the following items can be exemplified as parameters affecting the measurement.

(1) A polarization characteristic of the epidermis specific to a human body or a measurement position (2) An irradiation angle of illumination (3) A phase of illumination light (4) Position dependence of an incident angle of light due to unevenness of the epidermis Here, when a tip of the light blocking member 22 is made contact with the object 11 during imaging and the imaging device is kept without being moved, positions of a sulcus cutis and a crista cutis relative to the camera can be settled (fixed). In other words, a position and a site to be measured can be fixed. As a result, changes and fluctuations in the parameter (2) and the parameter (4) can be suppressed. In addition, prior to imaging the object, a sort of calibration regarding the arrangement angles and the revolution angles of the polarizer and the spatial light modulator relative to the camera and the light source is carried out, whereby a change and a fluctuation in the parameter (1) can be suppressed. Besides, operation of the spatial light modulator, the arrangement angles, a relationship of the arrangement angles between the polarizer and the spatial light modulator, and the like are controlled, which means that the parameter (3) is controlled. Consequently, a large amount of reflected light is caught such that a reflection characteristic and a scattering characteristic can be worked out, while a large amount of subsurface scattered light is caught such that a subsurface scattering characteristic can be worked out.

Specifically, the imaging method according to the first embodiment relates to the imaging method according to the first A mode of the disclosure. That is, in the imaging method according to the first embodiment, the object 11 is first imaged with the camera 31 while the polarizer 35 and the spatial light modulator 40A are rotated with respect to the camera 31 and the light source 32 in a state where the revolution angle (the revolution angle at the calibration) $\theta'$ is fixed. Subsequently, the optimum arrangement angle of the polarizer 35 relative to the camera 31 and the light source 32 is determined such that the optimum reflection characteristic of the object 11 is obtained. Specifically, for example, the object 11 is imaged while the polarizer 35 and the spatial light modulator 40A are rotated with respect to the camera 31 and the light source 32 in a state where the revolution angle $\theta'$ is fixed, where the revolution angle $\theta'$ is assumed as zero degrees, to obtain a large number of images (e.g., four images; specifically, images obtained at the setting at zero degrees, 45 degrees, 90 degrees, and 135 degrees relative to a reference position). Thereafter, the optimum arrangement angle $\zeta_0$ of the polarizer 35 and the spatial light modulator 40A relative to the camera 31 and the light source 32 is worked out from an average value of light intensities among the respective images (assumed as $I_{Cal-0}$, $I_{Cal-45}$, $I_{Cal-90}$, and $I_{Cal-135}$). In other words, for example, an angle at which the highest contrast can be obtained in an image is worked out as the optimum arrangement angle $\zeta_0$. Generally known methods can be employed as these procedures of processing. Following this, the object 11 is imaged with the camera 31 while the revolution angle $\theta$ is changed in a state where the polarizer 35 and the spatial light modulator 40A are fixed at the optimum arrangement angle $\zeta_0$. Specifically, a value of the revolution angle $\theta$ is changed to, for example, 0 degrees, 45 degrees, 90 degrees, and 135 degrees.

Change in light intensity (degree of polarization)=
$(I_{Cal-0}-I_{Cal-90})^{1/2}+(I_{Cal-45}-I_{Cal-135})/(I_{Cal-0}+I_{Cal-45}+I_{Cal-90}+I_{Cal-135})/2$ Specifically, the polarizer 35 and the spatial light modulator 40A are put into a state of being fixed at the optimum arrangement angle $\zeta_0$. In addition, in the imaging device 10A according to the first embodiment, the polarization plane of light emitting from the light source 32 and passing through the polarizer 35 (refer to the arrow "B") matches the incident light polarization plane of incident light entering the spatial light modulator 40A (refer to the arrow "C") and additionally, matches the optimum arrangement angle $\zeta_0$ as well (refer to the arrow "A"). In other words, a direction of the arrow "A", a direction of the arrow "B", and a direction of the arrow "C" in FIG. 2A, FIG. 2B, FIG. 2C, and FIG. 2D match each other. Meanwhile, the emitting light polarization plane of emitting light emitting from the spatial light modulator 40A is indicated by the arrow "E".

Figure 2A:
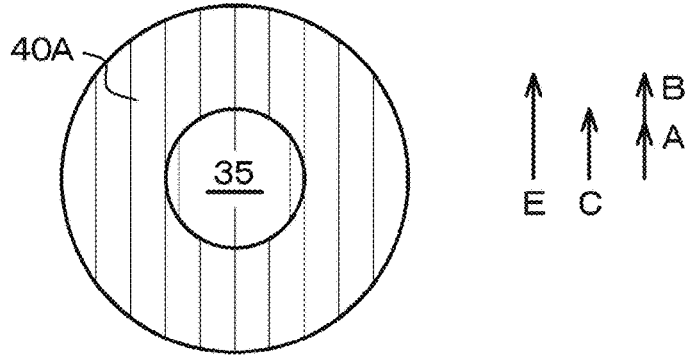
FIG. 2A, FIG. 2B, FIG. 2C, and FIG. 2D are conceptual diagrams each illustrating an arrangement state of the polarizer and the spatial light modulator when the spatial light modulator is rotated in the imaging device according to the first embodiment.

In this state, the object 11 is first imaged by setting the value of the revolution angle $\theta$ to zero degrees (refer to FIG. 2A). Because the revolution angle $\theta$=zero degrees is set, the emitting light polarization plane (refer to the arrow "E") is parallel to the incident light polarization plane (refer to the arrow "C"). Next, a voltage applied between the first electrode and the second electrode is changed to change the array of liquid crystal molecules in the liquid crystal layer and then, the revolution angle θ=45 degrees (refer to FIG. 2B), the revolution angle θ=90 degrees (refer to FIG. 2C), and the revolution angle θ=135 degrees (refer to FIG. 2D) are set to image the object 11 with the camera 31 at the respective revolution angles θ. Imaging conditions and so on for the object 11 described above are set forth in table 1 below.

TABLE 1

UNIT: DEGREE

Figure 2B:
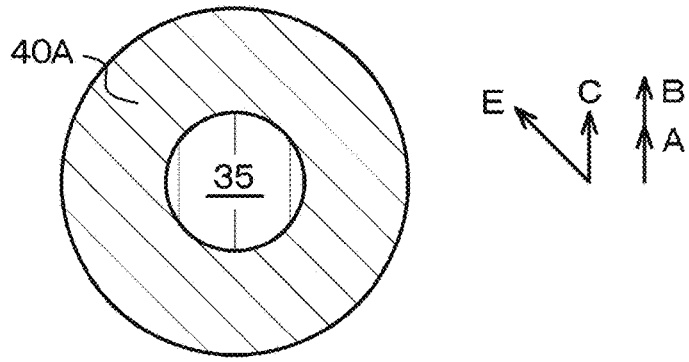
Figure 2C:
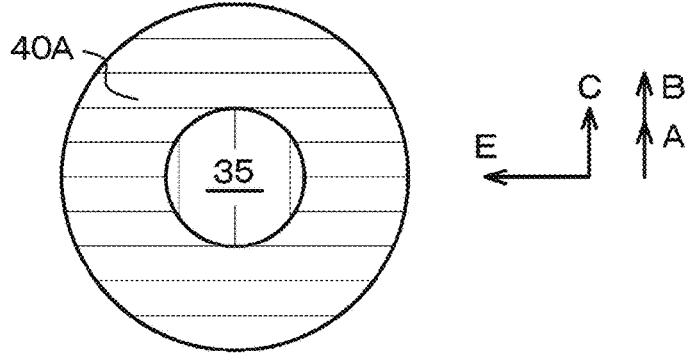
Figure 2D:
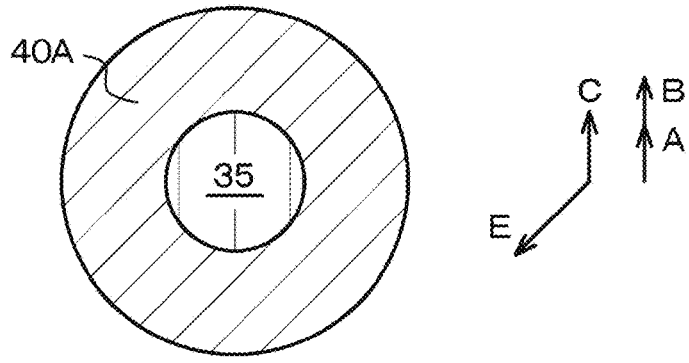

| | FIG. 2A | FIG. 2B | FIG. 2C | FIG. 2D |
|---|---|---|---|---|
| θ | 0 | 45 | 90 | 135 |
| $\xi_{in}$ | 0 | 0 | 0 | 0 |
| $\xi_{out}$ | 0 | 45 | 90 | 135 |
| $\zeta_{in}$ | 0 | 0 | 0 | 0 |
| $\zeta_{out}$ | 0 | 45 | 90 | 135 |

Here, because the polarization state of reflected light when light serving as the linearly polarized light is reflected on the surface of the epidermis is approximately the linearly polarized light, in the states illustrated in FIG. 2A, FIG. 2B, FIG. 2C, and FIG. 2D, light serving as the linearly polarized light in the direction of the arrow "E" is reflected on the surface of the epidermis to pass through the polarizer 35 and in the last place, a component in the direction of the arrow "B" reaches the camera 31. Note that the light intensities of the component of light in the direction of the arrow "B" in the states illustrated in FIG. 2A, FIG. 2B, FIG. 2C, and FIG. 2D are indicated by $I_{Ref-0}$, $I_{Ref-45}$, $I_{Ref-90}$, and $I_{Ref-135}$, respectively. Meanwhile, the polarization state of scattered light when light serving as the linearly polarized light is scattered at the inside of the epidermis and emits from the epidermis is, for example, the elliptically polarized light. Accordingly, light serving as the linearly polarized light in the direction of the arrow "E" in the states illustrated in FIG. 2A, FIG. 2B, FIG. 2C, and FIG. 2D is scattered at the inside of the epidermis to emit from the epidermis and then passes through the polarizer 35. In the last place, the component in the direction of the arrow "B" reaches the camera 31. The light intensities of the component of light in the direction of the arrow "B" in the states illustrated in FIG. 2A, FIG. 2B, and FIG. 2D are indicated by $I_{Sca-0}$, $I_{Sca-45}$, $I_{Sca-90}$, and $I_{Sca-135}$, respectively. The light intensities $I_0$, $I_{45}$, $I_{90}$, and $I_{135}$ in the states illustrated in FIG. 2A, FIG. 2B, and FIG. 2D, respectively, are as follows.

The state of the revolution angle θ=zero degrees (refer to FIG. 2A): $I_0 = I_{Ref-0} + I_{Sca-0}$ The state of the revolution angle θ=45 degrees (refer to FIG. 2B): $I_{45} = I_{Ref-45} + I_{Sca-45}$ The state of the revolution angle θ=90 degrees (refer to FIG. 2C): $I_{90} = I_{Ref-90} + I_{Sca-90}$ The state of the revolution angle θ=135 degrees (refer to FIG. 2D): $I_{135} = I_{Ref-135} + I_{Sca-135}$ Subsequently, data regarding the reflected light reflected on the surface of the epidermis and data regarding the scattered light scattered at the inside of the epidermis can be worked out from data for these light intensities $I_0$, $I_{45}$, $I_{90}$, and $I_{135}$. Specifically, image data at a revolution angle $θ_{max}$ at which the maximum light intensity is obtained corresponds to image data $ID_{max}$ based on the reflected light reflected on the surface of the epidermis and the scattered light scattered at the inside of the epidermis. In addition, image data $ID_{max\_90}$ at a revolution angle $θ_{max\_90}$ obtained by a revolution by 90 degrees with respect to the revolution angle $θ_{max}$ substantially corresponds to image data based on the scattered light scattered at the inside of the epidermis.

Accordingly, by subtracting the image data $ID_{max\_90}$ from the image data $ID_{max}$, image data based on the reflected light reflected on the surface of the epidermis can be obtained. Thereafter, an image based on the reflected light reflected on the surface of the epidermis and an image based on the scattered light scattered at the inside of the epidermis are simply generated from these items of the image data to be displayed on the monitor. Fundamentally, similar processing can be done also in the second embodiment or the third embodiment through the eighth embodiment described later.

When the imaging device according to the first embodiment or the second embodiment through the eighth embodiment described later is used to capture an image on the basis of, for example, the reflected light reflected on the surface of the epidermis (skin), a surface state of the skin such as skin roughness and texture of skin can be observed. Meanwhile, when an image is captured on the basis of the scattered light scattered at the inside of the epidermis (skin), an inner state of the skin such as a spot and dullness can be observed. Additionally, the polarizer arranged between the camera plus the light source and the object, and the spatial light modulator arranged between the polarizer and the object to control the revolution angle of the emitting light polarization plane relative to the incident light polarization plane are provided. As a result, although the configuration and the structure are simple, the polarization state of light with which the object is irradiated can be optimized in accordance with the object.

Besides, in the imaging device according to the first embodiment or the second embodiment described later, the revolution angle θ (optical rotation characteristic) is controlled through voltage control in the liquid crystal device. Accordingly, it is possible to obtain a state where the polarizer and the spatial light modulator are fixed with respect to the camera and the light source while the object is imaged. In other words, it is not necessary to change a position of an optical system for illuminating the object and measuring the object. Therefore, the optical rotation characteristic of the object can be further accurately measured in detail.

Second Embodiment

Figure 3A:
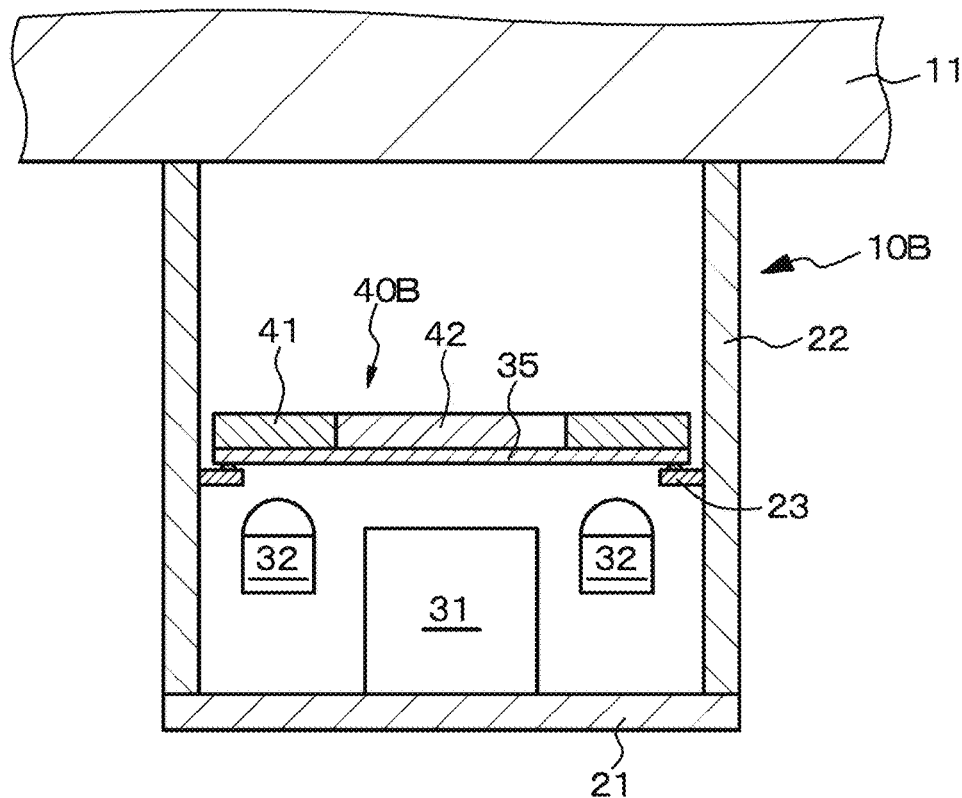
FIG. 3A, FIG. 3B, and FIG. 3C are conceptual diagrams of an imaging device, a spatial light modulator, and a polarizer, respectively, according to a second embodiment.
Figure 3B:
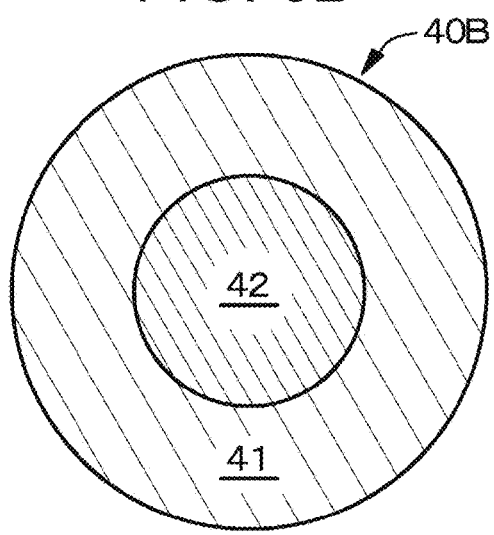
Figure 3C:
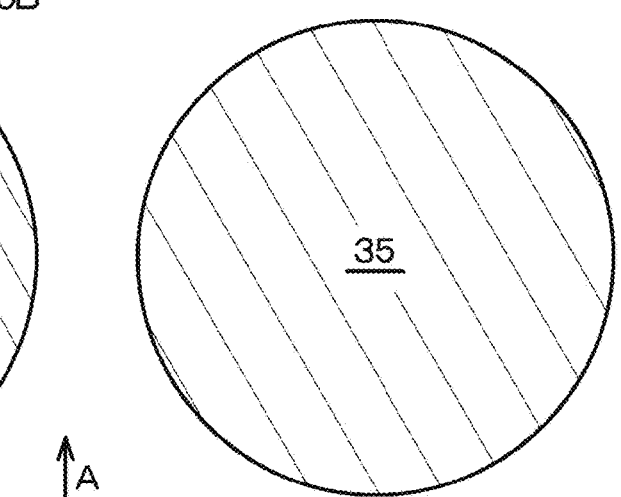

The second embodiment is a modification of the first embodiment and specifically relates to the imaging device according to the first A-2 mode of the disclosure and the imaging method according to the first B mode of the disclosure. A conceptual diagram of the imaging device according to the second embodiment is illustrated in FIG. 3A, a conceptual diagram of a spatial light modulator is illustrated in FIG. 3B, and a conceptual diagram of a polarizer 35 is illustrated in FIG. 3C. In addition, the polarization state at the spatial light modulator when the spatial light modulator is operated in the imaging device according to the second embodiment is illustrated in each of conceptual diagrams in FIG. 4A, FIG. 4B, FIG. 4C, and FIG. 4D.

In the imaging device 10B according to the second embodiment, the spatial light modulator 40B is constituted by an annular-shaped first region 41 and a second region 42 positioned on an inner side of the first region 41. Additionally, light emitting from a light source 32 and passing through the polarizer 35 and the first region 41 of the spatial light modulator 40B to collide with an object 11 reaches a camera 31 after passing through the second region 42 of the spatial light modulator 40B and the polarizer 35. The polarizer 35 and the spatial light modulator 40B are fixed with respect to the camera 31 and the light source 32. Furthermore, when a value of an angle formed by the incident light polarization plane at the first region 41 of the spatial light modulator 40B and the emitting light polarization plane at the second region 42 of the spatial light modulator 40B is assumed as ψ (in degree) and a value of an angle formed by the emitting light polarization plane at the first region 41 of the spatial light modulator 40B and the emitting light polarization plane at the second region 42 of the spatial light modulator 40B is assumed as ψ' (in degree), a revolution angle θ at the first region 41 of the spatial light modulator 40B is changed by controlling operation of the first region 41 of the spatial light modulator 40B such that ψ' is set to ψ and a value different from ψ. More specifically, ψ'=ψ, ψ'=(ψ+45), ψ'=(ψ+90), and ψ'=(ψ+135) are set and furthermore, ψ=0 is set.

In the imaging method according to the second embodiment, the object 11 is first imaged with the camera 31 while a revolution angle (a revolution angle at the calibration) θ' is changed (e.g., θ'=zero degrees, 45 degrees, 90 degrees, and 135 degrees) in a state where the polarizer 35 and the spatial light modulator 40B are fixed with respect to the camera 31 and the light source 32 and then, the optimum revolution angle relative to the camera 31 and the light source 32 is determined such that the optimum reflection characteristic of the object 11 is obtained. Here, the optimum revolution angle is specifically assumed as ψ. Subsequently, in a state where the polarizer 35 and the spatial light modulator 40B are fixed with respect to the camera 31 and the light source 32, the object 11 is imaged with the camera 31 by setting the revolution angle θ to the optimum revolution angle and a value different from the optimum revolution angle.

Specifically, the revolution angle of the spatial light modulator 40B is put into a state of being fixed at the optimum revolution angle. Specifically, a direction of the transmission axis of the polarizer 35 (refer to the arrow "B") and a direction of the optimum revolution angle (refer to the arrow "A") form the angle ψ and these directions (refer to the arrow "A" and the arrow "B") are fixed. In addition, the incident light polarization plane at the first region 41 of the spatial light modulator 40B (refer to the arrow "C") and the emitting light polarization plane at the second region 42 of the spatial light modulator 40B (refer to the arrow "F") are fixed as well. In this state, the object 11 is imaged by setting the value of the revolution angle θ to zero degrees (refer to FIG. 4A). The revolution angle θ=zero degrees is set and the emitting light polarization plane (refer to the arrow "E") is parallel to the incident light polarization plane (refer to the arrow "C"). Next, a voltage applied between a first electrode and a second electrode is changed to change an array of liquid crystal molecules in a liquid crystal layer and then, the revolution angle θ=45 degrees (refer to FIG. 4B), the revolution angle θ=90 degrees (refer to FIG. 4C), and the revolution angle θ=135 degrees (refer to FIG. 4D) are set to image the object 11 with the camera 31 at the respective revolution angles θ. Imaging conditions and so on for the object 11 described above are set forth in table 2 below.

TABLE 2

Figure 4A:
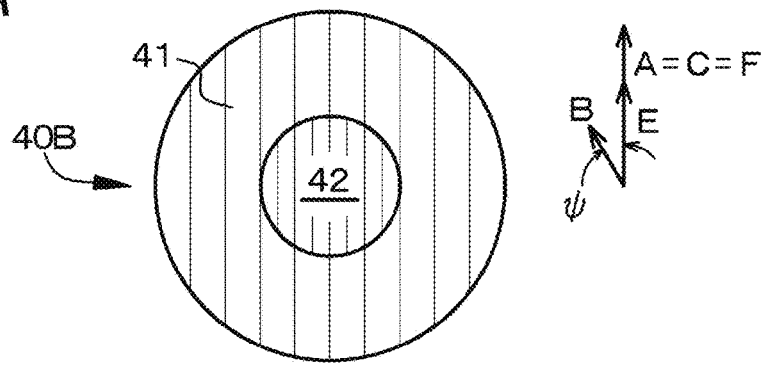
FIG. 4A, FIG. 4B, FIG. 4C, and FIG. 4D are conceptual diagrams each illustrating a polarization state at the spatial light modulator when the spatial light modulator is operated in the imaging device according to the second embodiment.
Figure 4B:
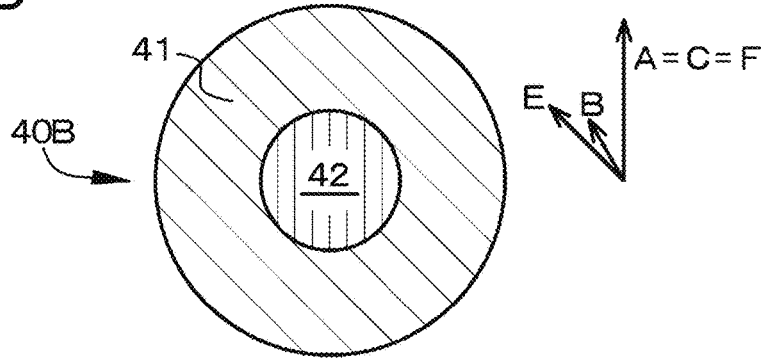
Figure 4C:
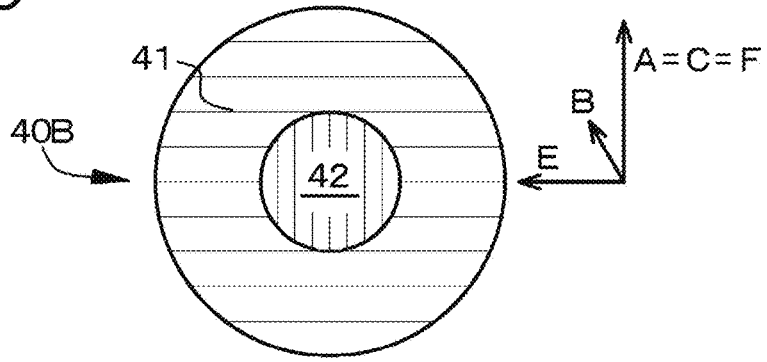
Figure 4D:
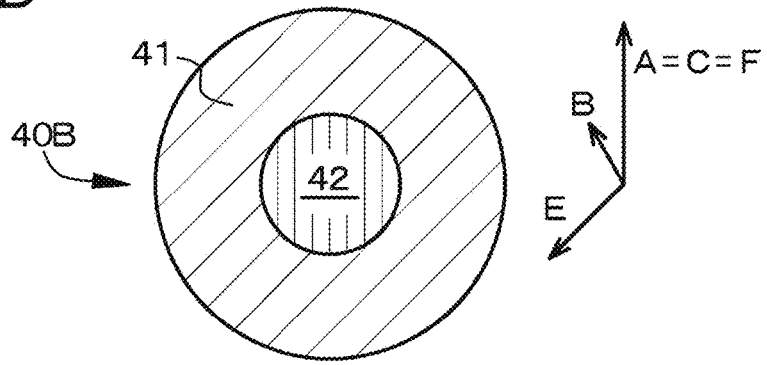

| | FIG. 4A | FIG. 4B | FIG. 4C | FIG. 4D |
|---|---|---|---|---|
| | | | | UNIT: DEGREE |
| θ | 0 | 45 | 90 | 135 |
| $\zeta_{in}$ | $\zeta_0$ | $\zeta_0$ | $\zeta_0$ | $\zeta_0$ |
| $\zeta_{out}$ | $-\zeta_0$ | $45-\zeta_0$ | $90-\zeta_0$ | $135-\zeta_0$ |

TABLE 2-continued

| | FIG. 4A | FIG. 4B | FIG. 4C | FIG. 4D |
|---|---|---|---|---|
| | | | | UNIT: DEGREE |
| $\zeta_{in}$ | 0 | 0 | 0 | 0 |
| $\zeta_{out}$ | 0 | 45 | 90 | 135 |
| ψ | 0 | 0 | 0 | 0 |
| ψ' | 0 | 45 | 90 | 135 |

In the imaging device according to the second embodiment, it is made possible to independently control the emitting light polarization plane at the first region 41 of the spatial light modulator 40B and the emitting light polarization plane at the second region 42 of the spatial light modulator 40B and thus, for example, texture of skin and the optical rotation characteristic of skin can be measured while the highest contrast is obtained.

Third Embodiment

Figure 5A:
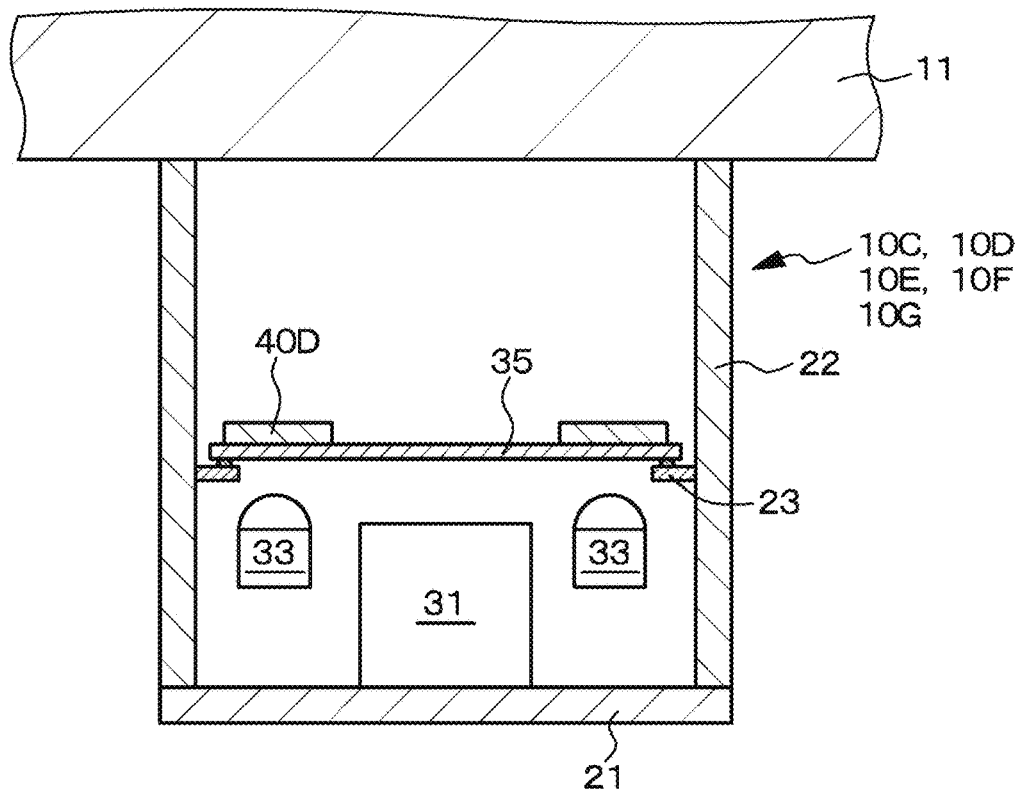
Figure 5B:
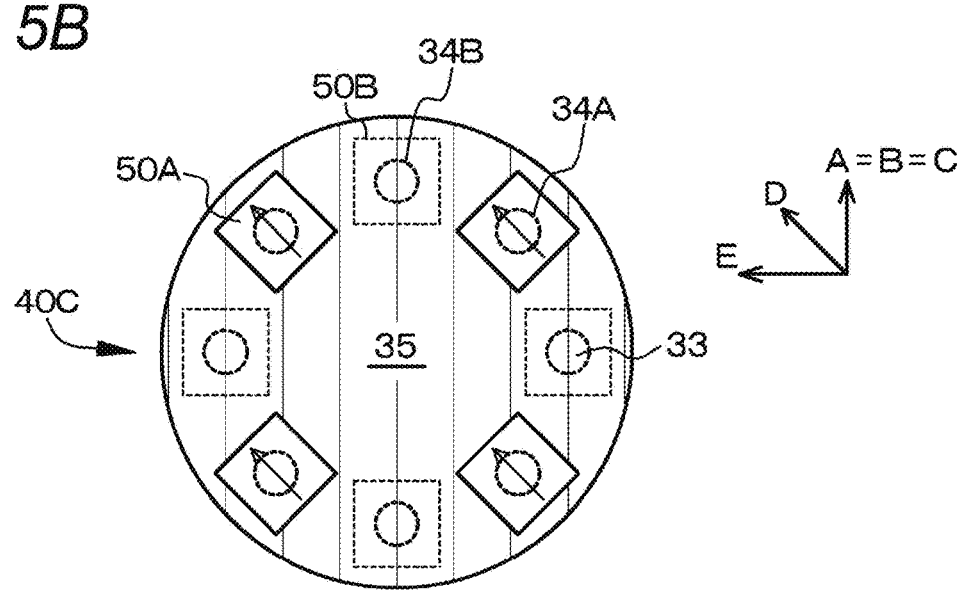
FIG. 5B is a conceptual diagram illustrating an arrangement state of a polarizer and a spatial light modulator (½-wave plate) in the imaging device according to the third embodiment.

The third embodiment is also a modification of the first embodiment and relates to the imaging device according to the first B mode of the disclosure, specifically, the imaging device according to the first B-1 mode of the disclosure, in which one unit of ½-wave plates is provided. In addition, the third embodiment relates to the imaging method according to the second mode of the disclosure. A conceptual diagram of the imaging device according to the third embodiment or the fourth embodiment through the seventh embodiment described later is illustrated in FIG. 5A. In addition, a conceptual diagram of an arrangement state of the polarizer 35 and the spatial light modulator (½-wave plate 50A) in the imaging device according to the third embodiment is illustrated in FIG. 5B. The light source 33 according to the third embodiment or the fourth embodiment through the seventh embodiment described later is constituted by a plurality of illumination means that illuminates a desired region of the spatial light modulator. Here, the illumination means are formed by light emitting units 34A and 34B (specifically, light emitting elements such as light emitting diodes (LEDs)).

In the imaging device 10C according to the third embodiment, light emitting from the light source 33 (specifically, the light emitting unit 34A) and passing through the polarizer 35 and the spatial light modulator 40C to collide with the object 11 reaches the camera 31 after passing through the polarizer 35. Additionally, the light source 33 is constituted by the plurality of light emitting units 34A and 34B (specifically, the LEDs as described above) arranged apart from one another. Meanwhile, the spatial light modulator 40C is formed by the ½-wave plate 50A that transmits light emitting from each of some 34A of the plurality of light emitting units 34A and 34B. A value of an angle φ formed by the optical axis of the ½-wave plate 50A and the incident light polarization plane is not zero degrees. Specifically, the polarizer 35 and the ½-wave plate 50A are fixed with respect to the camera 31 and the light source 33 and the value of the angle φ is 45 degrees. In addition, light emitting from the light emitting unit 34B passes through the polarizer 35 to collide with the object 11 and passes through the polarizer 35 one more time to reach the camera 31. The reference numerals 50A and 51B represent regions in the polarizer when light emitting from the light emitting unit 34B passes through the polarizer 35.

The imaging method according to the third embodiment or the fourth embodiment through the seventh embodiment described later is, as described above, an imaging method using the imaging device 10C, 10D, 10E, 10F, or 10G provided with the camera 31, the light source 33 constituted by the plurality of light emitting units 34A and 34B arranged apart from one another, the polarizer 35 arranged between the camera 31 plus the light source 33 and the object 11, and the ½-wave plate 50A, 51A, 52A, 52B, 52C, 52D, 53A, 53B, 54A, or 54B arranged between the polarizer 35 and the object 11 to transmit light emitting from each of at least some 34A of the plurality of light emitting units 34A and 34B (both of the light emitting units 34A and 34B depending on cases). Additionally, the object 11 is imaged with the camera 31 while the ½-wave plate 50A, 51A, 52A, 52B, 52C, 52D, 53A, 53B, 54A, or 54B and the polarizer 35 are arranged such that the value of the angle φ formed by the optical axis of the ½-wave plate 50A, 51A, 52B, 52C, 52D, 53A, 53B, 54A, or 54B and the transmission axis of the polarizer 35 is set to a value other than zero degrees.

Specifically, in the imaging method according to the third embodiment, the object 11 is first imaged with the camera 31 while the polarizer 35 and the ½-wave plate 50A are rotated with respect to the camera 31 and the light source 33 and then, the optimum arrangement angle $\zeta_0$ of the polarizer 35 and the ½-wave plate 50A relative to the camera 31 and the light source 33 (refer to the arrow "A", the arrow "B", and the arrow in FIG. 5B) is determined such that the optimum reflection characteristic of the object 11 is obtained. Subsequently, in this state, the light emitting unit 34B is caused to emit light and the object 11 is imaged with the camera 31. Thereafter, the light emitting unit 34A is caused to emit light and the object 11 is imaged with the camera 31. States of the object 11 when the object 11 is illuminated at $\zeta_{out}$=zero degrees and $\zeta_{out}$=90 degrees can be imaged in this manner. Imaging conditions and so on for the object 11 are set forth in table 3 below.

TABLE 3

| ½-WAVE PLATE REGION OF POLARIZER | 50A | UNIT: DEGREE 50B |
|---|---|---|
| θ | 90 | 0 |
| φ | 45 | — |
| $\xi_{in}$ | 0 | — |
| $\xi_{out}$ | 90 | — |
| $\zeta_{in}$ | 0 | 0 |
| $\zeta_{out}$ | 90 | 0 |

Fourth Embodiment

The fourth embodiment is a modification of the third embodiment and relates to the imaging device according to the first B-2 mode of the disclosure and the imaging method according to the second A mode of the disclosure. The conceptual diagram of the imaging device according to the fourth embodiment is as illustrated in FIG. 5A. In addition, a conceptual diagram of an arrangement state of the polarizer 35 and the spatial light modulator (½-wave plate) when the polarizer 35 and the spatial light modulator (½-wave plate) are rotated in the imaging device according to the fourth embodiment is illustrated in each of FIG. 6A, FIG. 6B, FIG. 7A, and FIG. 7B.

In the imaging device 10D according to the fourth embodiment, the polarizer 35 is arranged rotatably with respect to the camera 31 and the light source 33, while the ½-wave plate 51A is fixed with respect to the polarizer 35. Additionally, the value of the angle φ is 45 degrees. Furthermore, the plurality of ½-wave plates 51A is arranged in an annular shape and the polarizer 35 (including the ½-wave plates 51A) is arranged at a position at zero degrees, a position at 45 degrees, a position at 90 degrees, and a position at 135 degrees with respect to the optimum arrangement angle $\zeta_0$ of the polarizer 35 relative to the camera 31 and the light source 33.

In the imaging method according to the fourth embodiment, the object 11 is first imaged with the camera 31 while the polarizer 35 and the ½-wave plate 51A are rotated with respect to the camera 31 and the light source 33 and also the light emitting unit 34B is caused to emit light and then, the optimum arrangement angle $\zeta_0$ of the polarizer 35 and the ½-wave plate 51A relative to the camera 31 and the light source 33 (refer to the arrow "A") is determined such that the optimum reflection characteristic of the object 11 is obtained. Subsequently, the object 11 is imaged with the camera 31 while the polarizer 35 and the ½-wave plate 51A are rotated (refer to the arrow "B", the arrow "C", the arrow "D", and the arrow "E") by using the optimum arrangement angle $\zeta_0$ as a reference (refer to the arrow "A"). Here, the value of the angle φ is set to 45 degrees. In addition, the plurality of ½-wave plates 51A is arranged in an annular shape.

Figure 6A:
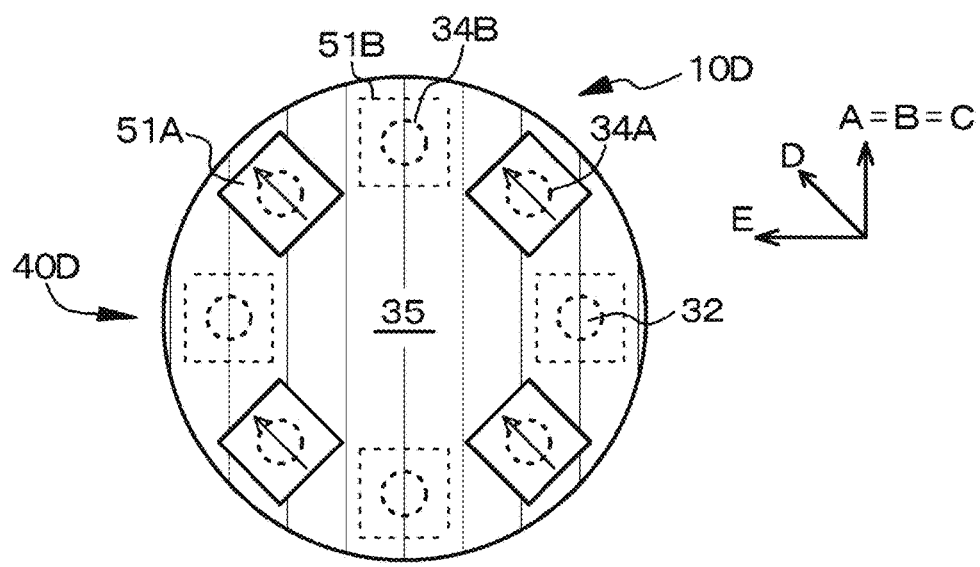
FIG. 6A and FIG. 6B are conceptual diagrams each illustrating an arrangement state of a polarizer and a spatial light modulator (½-wave plate) when the polarizer and the spatial light modulator (½-wave plate) are rotated in the imaging device according to the fourth embodiment.

Specifically, the object 11 is imaged with the camera 31 while the polarizer 35 is arranged at a position at a position at zero degrees with respect to the optimum arrangement angle $\zeta_0$ and also the light emitting unit 34A is caused to emit light; thereafter, the object 11 is imaged with the camera 31 while the light emitting unit 34B is caused to emit light (refer to FIG. 6A). Subsequently, the object 11 is imaged with the camera 31 while the polarizer 35 is arranged at a position at a position at 45 degrees with respect to the optimum arrangement angle $\zeta_0$ and also the light emitting unit 34A is caused to emit light; thereafter, the object 11 is imaged with the camera 31 while the light emitting unit 34B is caused to emit light (refer to FIG. 6B). Furthermore, the object 11 is imaged with the camera 31 while the polarizer 35 is arranged at a position at a position at 90 degrees with respect to the optimum arrangement angle $\zeta_0$ and also the light emitting unit 34A is caused to emit light; thereafter, the object 11 is imaged with the camera 31 while the light emitting unit 34B is caused to emit light (refer to FIG. 7A). Besides, the object 11 is imaged with the camera 31 while the polarizer 35 is arranged at a position at a position at 135 degrees with respect to the optimum arrangement angle $\zeta_0$ and also the light emitting unit 34A is caused to emit light; thereafter, the object 11 is imaged with the camera 31 while the light emitting unit 34B is caused to emit light (refer to FIG. 7B). Imaging conditions and so on for the object 11 are set forth in table 4 below.

TABLE 4

Figure 6B:
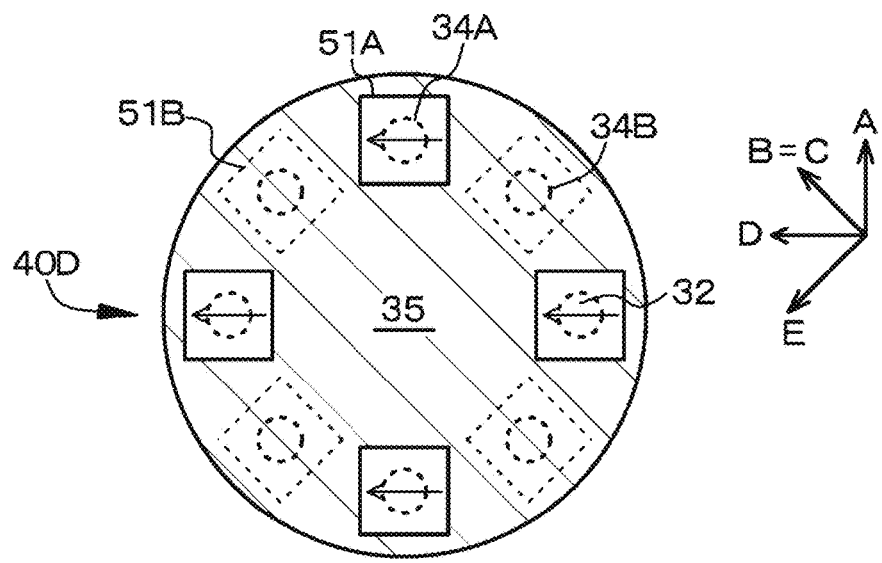
Figure 7A:
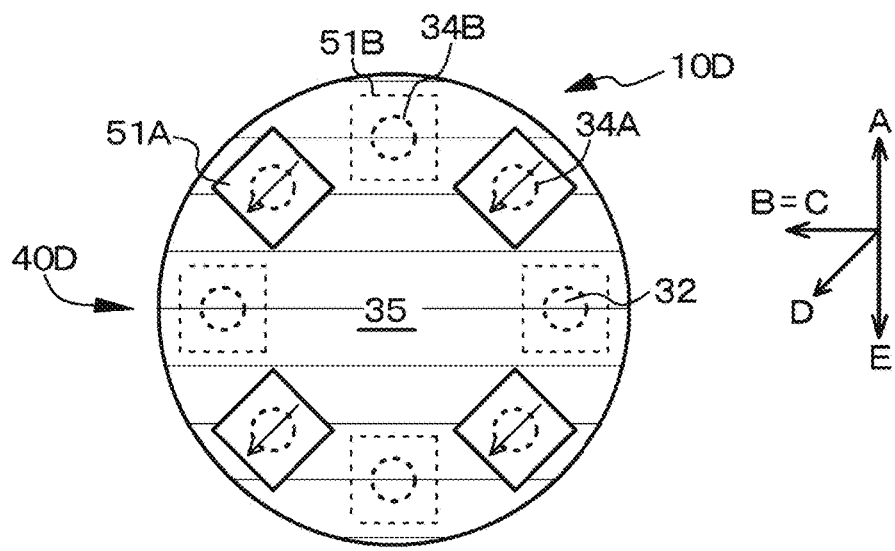
FIG. 7A and FIG. 7B are conceptual diagrams each illustrating an arrangement state of the polarizer and the spatial light modulator (½-wave plate) when the polarizer and the spatial light modulator (½-wave plate) are rotated in the imaging device according to the fourth embodiment.
Figure 7B:
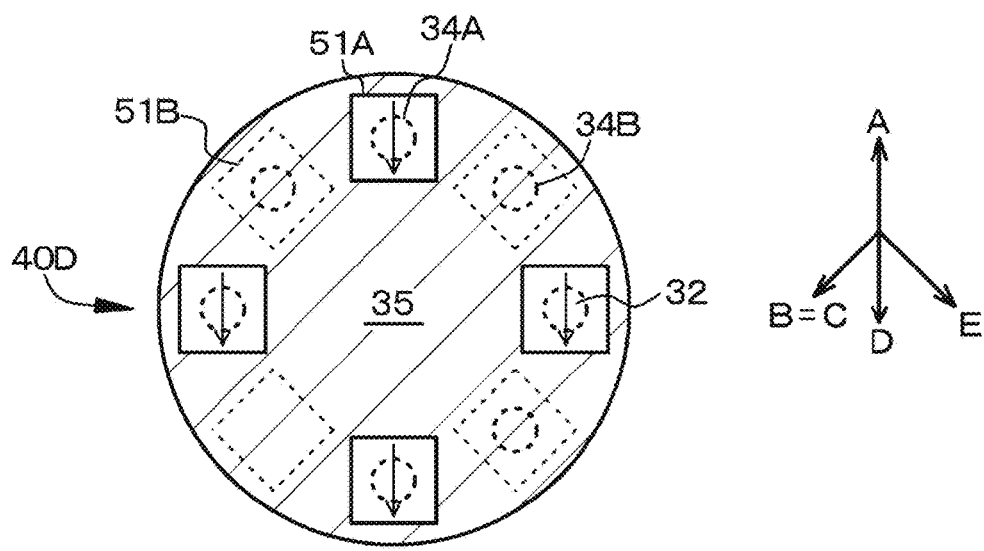

| | FIG. 6A | FIG. 6B | FIG. 7A | UNIT: DEGREE FIG. 7B |
|---|---|---|---|---|
| θ | 90 | 90 | 90 | 90 |
| φ | 45 | 45 | 45 | 45 |
| $\xi_{in}$ | 0 | 0 | 0 | 0 |
| $\xi_{out}$ | 90 | 90 | 90 | 90 |
| $\zeta_{in}$ | 0 | 45 | 90 | 135 |
| $\zeta_{out}$ | 90 | 135 | 180 | 225 |

Fifth Embodiment

The fifth embodiment is also a modification of the third embodiment and relates to the imaging device according to the first C mode of the disclosure, more specifically, the imaging device according to the first C-1 mode of the disclosure, in which a plurality of units of the ½-wave plates is provided. In addition, the fifth embodiment relates to the imaging method according to the second B mode of the disclosure, more specifically, the imaging method according to the second B-1 mode of the disclosure. A conceptual diagram of an arrangement state of the polarizer 35 and the spatial light modulator (½-wave plate) in the imaging device according to the fifth embodiment is illustrated in FIG. 8.

In the imaging device 10E according to the fifth embodiment, the light source 33 is constituted by a plurality of light emitting units 34 arranged apart from one another. In addition, the spatial light modulator 40E is formed by M number of ½-wave plate groups, each of which is constituted by the ½-wave plates 52A, 52B, 52C, or 52D that transmit light emitting from each of the plurality of light emitting units 34. Furthermore, when a value of an angle formed by the incident light polarization plane and the optical axis of the ½-wave plate 52A in a first ½-wave plate group, which transmits light from a first light source group 34A, is assumed as $\phi_1$ and a value of an angle formed by the incident light polarization plane and the optical axis of the ½-wave plate in an mth ½-wave plate group (the ½-wave plate 52B when m=2 is set; the ½-wave plate 52C when m=3 is set; the ½-wave plate 52D when m=4 is set), which transmits light from an mth light source group 34B, 34C, or 34D (where m=2, 3, . . . , M), is assumed as $\phi_1=0$ (in degree)

$|\phi_m-\phi_{m-1}|=\phi_0$ are satisfied. Here, the polarizer 35 and the ½-wave plates 52A, 52B, 52C, and 52D are fixed with respect to the camera 31 and the light source 33 and in the fifth embodiment, M=4 and $\phi_0$=22.5 degrees are set. A relationship between $\phi$ and $\theta$ and so on are set forth in table 5 below.

In the imaging method according to the fifth embodiment, the object 11 is imaged with the camera 31 while the polarizer 35 is rotated with respect to the camera 31 and the light source 33 using the aforementioned imaging device 10E according to the fifth embodiment and, after the optimum arrangement angle $\zeta_0$ of the polarizer 35 relative to the camera 31 and the light source 33 is determined such that the optimum reflection characteristic of the object 11 is obtained, the object 11 is imaged with the camera 31 while the light source 33 (light emitting unit 34) is caused to light up. Specifically, for example, the object 11 is imaged with the camera 31 while the polarizer 35 is arranged at the optimum arrangement angle $\zeta_0$.

In the illustrated example, the number of the ½-wave plates constituting the ½-wave plate groups is set to "four". However, the number is not limited to such a value. This is similarly applicable to the embodiments below.

TABLE 5

| ½ | 52A | 52B | 52C | UNIT: DEGREE 52D |
|---|---|---|---|---|
| $\theta$ | 0 | 45 | 90 | 135 |
| $\phi$ | 0 | 22.5 | 45 | 67.5 |
| $\xi_{in}$ | 0 | 0 | 0 | 0 |
| $\xi_{out}$ | 0 | 45 | 90 | 135 |

TABLE 5-continued

| ½ | 52A | 52B | 52C | UNIT: DEGREE 52D |
|---|---|---|---|---|
| $\xi_{in}$ | 0 | 0 | 0 | 0 |
| $\xi_{out}$ | 0 | 45 | 90 | 135 |

Sixth Embodiment

The sixth embodiment is also a modification of the third embodiment, relating to the imaging device according to the first C-2 mode of the disclosure and also relating to the imaging method according to the second B-2 mode of the disclosure. A conceptual diagram of an arrangement state of the polarizer 35 and the spatial light modulator (½-wave plates 53A and 53B) when the polarizer 35 and the spatial light modulator (½-wave plates 53A and 53B) are rotated in the imaging device according to the sixth embodiment is illustrated in each of FIG. 9A and FIG. 9B.

In the imaging device 10F according to the sixth embodiment, the polarizer 35 is arranged rotatably with respect to the camera 31 and the light source 33. Meanwhile, the ½-wave plates 53A and 53B are fixed with respect to the polarizer 35. Furthermore, the multiple ½-wave plates 53A and 53B are arranged in an annular shape and the polarizer 35 is arranged at a position at zero degrees and a position at 90 degrees with respect to the optimum arrangement angle $\zeta_0$ of the polarizer 35 relative to the camera 31 and the light source 33. In the sixth embodiment, M=2 and $\phi_0$=22.5 degrees are set.

In the imaging method according to the sixth embodiment, an image is captured using the imaging device 10F according to the sixth embodiment described above. Specifically, in the imaging method according to the sixth embodiment, the object 11 is first imaged with the camera 31 while the polarizer 35 and the ½-wave plates 53A and 53B are rotated with respect to the camera 31 and the light source 33 and also the light emitting unit 34A is caused to emit light and then, the optimum arrangement angle $\zeta_0$ of the polarizer 35 and the ½-wave plates 53A and 53B relative to the camera 31 and the light source 33 (refer to the arrow "A") is determined such that the optimum reflection characteristic of the object 11 is obtained. Subsequently, by using the optimum arrangement angle $\zeta_0$ as a reference (refer to the arrow "A"), the object 11 is imaged with the camera 31 while the light emitting unit 34A is caused to light up and thereafter, the object 11 is imaged with the camera 31 while the light emitting unit 34B is caused to light up (refer to FIG. 9A). Subsequently, the polarizer 35 and the ½-wave plates 53A and 53B are rotated by 90 degrees (refer to the arrow "B" and the arrow "C") and then, the object 11 is imaged with the camera 31 while the light emitting unit 34A is caused to light up. Thereafter, the object 11 is imaged with the camera 31 while the light emitting unit 34B is caused to light up (refer to FIG. 9B). Imaging conditions and so on for the object 11 are set forth in table 6 below.

TABLE 6

Figure 9A:
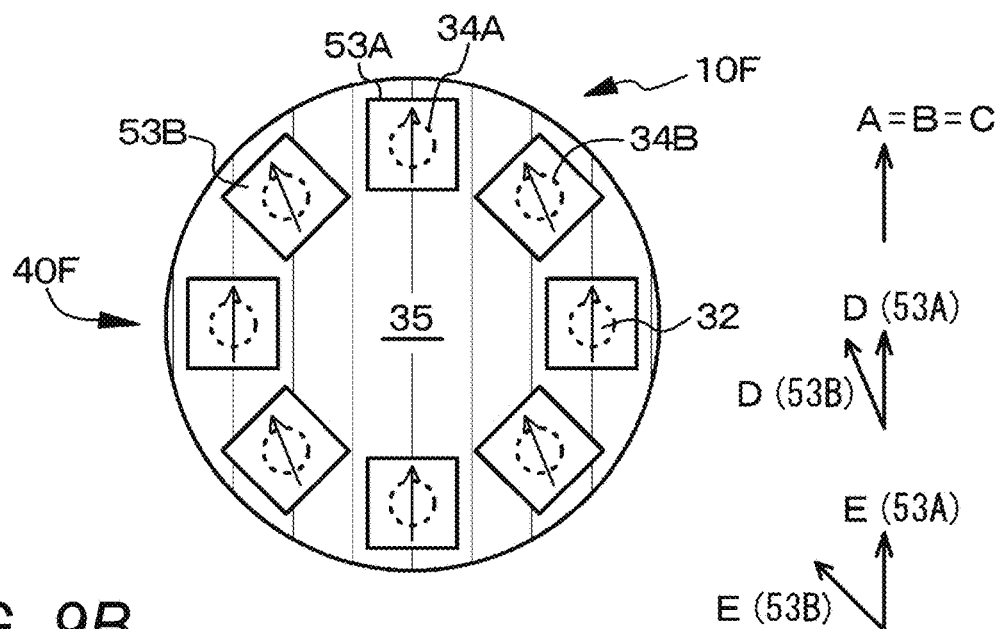
FIG. 9A and FIG. 9B are conceptual diagrams each illustrating an arrangement state of a polarizer and a spatial light modulator (½-wave plate) when the polarizer and the spatial light modulator (½-wave plate) are rotated in the imaging device according to the sixth embodiment.
Figure 9B:
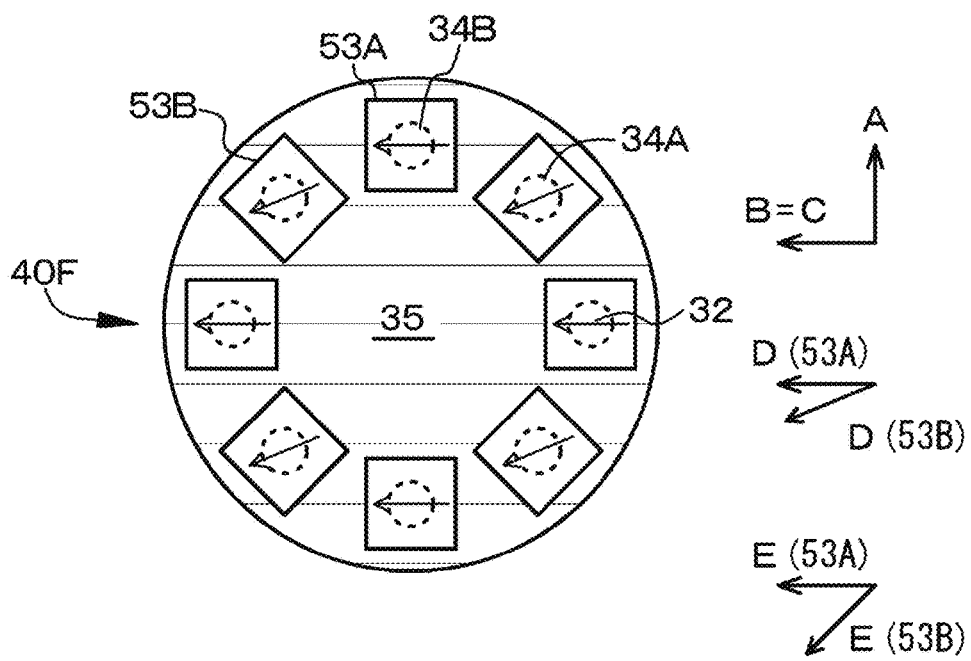

| | FIG. 9A | FIG. 9A | FIG. 9B | UNIT: DEGREE FIG. 9B |
|---|---|---|---|---|
| | ½-WAVE PLATE | | | |
| | 53A | 53B | 53A | 53B |
| $\theta$ | 0 | 45 | 0 | 45 |
| $\phi$ | 0 | 22.5 | 0 | 22.5 |
| $\xi_{in}$ | 0 | 0 | 0 | 0 |

TABLE 6-continued

|  | FIG. 9A | FIG. 9A ½-WAVE PLATE | FIG. 9B | UNIT: DEGREE FIG. 9B |
|---|---|---|---|---|
|  | 53A | 53B | 53A | 53B |
| $\xi_{out}$ | 0 | 45 | 0 | 45 |
| $\zeta_{in}$ | 0 | 0 | 90 | 90 |
| $\zeta_{out}$ | 0 | 45 | 90 | 135 |

Seventh Embodiment

The seventh embodiment is also a modification of the third embodiment, relating to the imaging device according to the first C-3 mode of the disclosure and also relating to the imaging method according to the second C mode of the disclosure. A conceptual diagram of an arrangement state of the polarizer 35 and the spatial light modulator (½-wave plates 54A and 54B) when the spatial light modulator (½-wave plates 54A and 54B) are rotated in the imaging device according to the seventh embodiment is illustrated in each of FIG. 10A and FIG. 10B.

In the imaging device 10G according to the seventh embodiment, the polarizer 35 is arranged rotatably with respect to the camera 31 and the light source 33. The ½-wave plates 54A and 54B are also arranged rotatably with respect to the polarizer 35. Additionally, the entire multiple ½-wave plates 54A and 54B are arranged in an annular shape, the polarizer 35 is arranged so as to be fixed at zero degrees with respect to the optimum arrangement angle $\zeta_0$ of the polarizer 35 relative to the camera 31 and the light source 33, and the entire ½-wave plates 54A and 54B are arranged at a position at zero degrees (½-wave plates 54A) or a position at 45 degrees (½-wave plates 54B). Furthermore, in the seventh embodiment, M=2 and $\phi_0$=22.5 degrees are set.

In the imaging method according to the seventh embodiment,

M number of ½-wave plate groups is provided, each of which is constituted by the plurality of ½-wave plates 54A or 54B arranged apart from one another, the polarizer 35 is arranged rotatably with respect to the camera 31 and the light source 33, and the entire ½-wave plates 54A and 54B are arranged rotatably with respect to the polarizer 35. Additionally, when a value of an angle formed by the incident light polarization plane and the optical axis of the ½-wave plate 54A in a first ½-wave plate group, which transmits light from a first light source group 34A, is assumed as $\phi_1$ and a value of an angle formed by the incident light polarization plane and the optical axis of the ½-wave plate in an mth ½-wave plate group, which transmits light from an mth light source group (where m=2, 3, . . . , M) 34B, is assumed as $\phi_1=0$ (in degree)

$|\phi_m-\phi_{m-1}|=\phi_0$ are satisfied.

In this state, in the imaging method according to the seventh embodiment, the object 11 is first imaged with the camera 31 while the polarizer 35 and the entire ½-wave plates 54A and 54B are rotated with respect to the camera 31 and the light source 33 and then, the optimum arrangement angle $\zeta_0$ of the polarizer 35 relative to the camera 31 and the light source 33 is determined such that the optimum reflection characteristic of the object 11 is obtained. Subsequently, the object 11 is imaged with the camera 31 while the entire ½-wave plates 54A and 54B are rotated in a state where the polarizer 35 is fixed at the optimum arrangement angle $\zeta_0$.

Specifically, in the imaging method according to the seventh embodiment, the object 11 is first imaged with the camera 31 while the polarizer 35 and the entire ½-wave plates 54A and 54B are rotated with respect to the camera 31 and the light source 33 and also the light emitting unit 34A is caused to emit light and then, the optimum arrangement angle $\zeta_0$ of the polarizer 35 and the ½-wave plates 54A and 54B relative to the camera 31 and the light source 33 (refer to the arrow "A") is determined such that the optimum reflection characteristic of the object 11 is obtained. Subsequently, by using the optimum arrangement angle $\zeta_0$ as a reference (refer to the arrow "A", the arrow "B", and the arrow "C"), the object 11 is imaged with the camera 31 while the light emitting unit 34A is caused to light up and thereafter, the object 11 is imaged with the camera 31 while the light emitting unit 34B is caused to light up (refer to FIG. 10A). Subsequently, the entire ½-wave plates 54A and 54B are rotated by 45 degrees and then, the object 11 is imaged with the camera 31 while the light emitting unit 34A is caused to light up. Thereafter, the object 11 is imaged with the camera 31 while the light emitting unit 34B is caused to light up (refer to FIG. 10B). Imaging conditions and so on for the object 11 are set forth in table 7 below.

TABLE 7

Figure 10A:
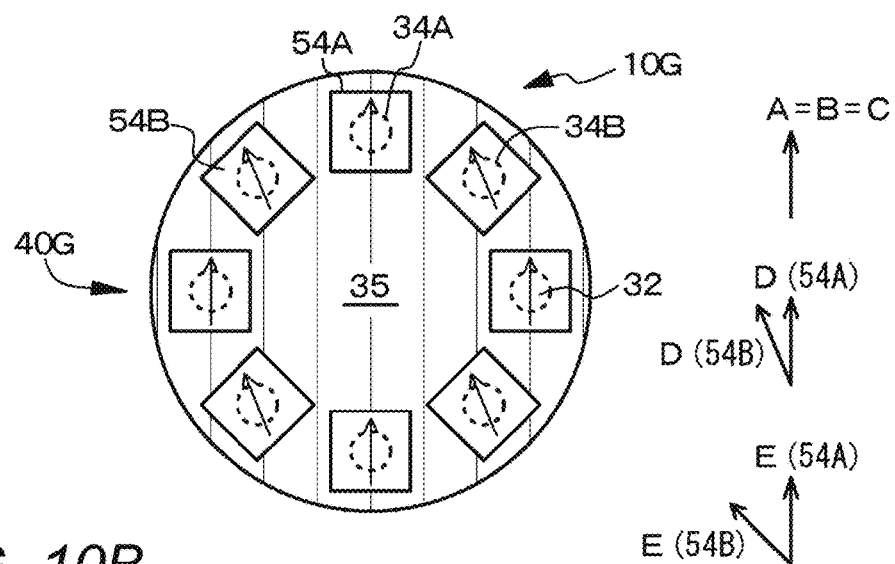
FIG. 10A and FIG. 10B are conceptual diagrams each illustrating an arrangement state of a polarizer and a spatial light modulator (½-wave plate) when the spatial light modulator (½-wave plate) is rotated in the imaging device according to the seventh embodiment.
Figure 10B:
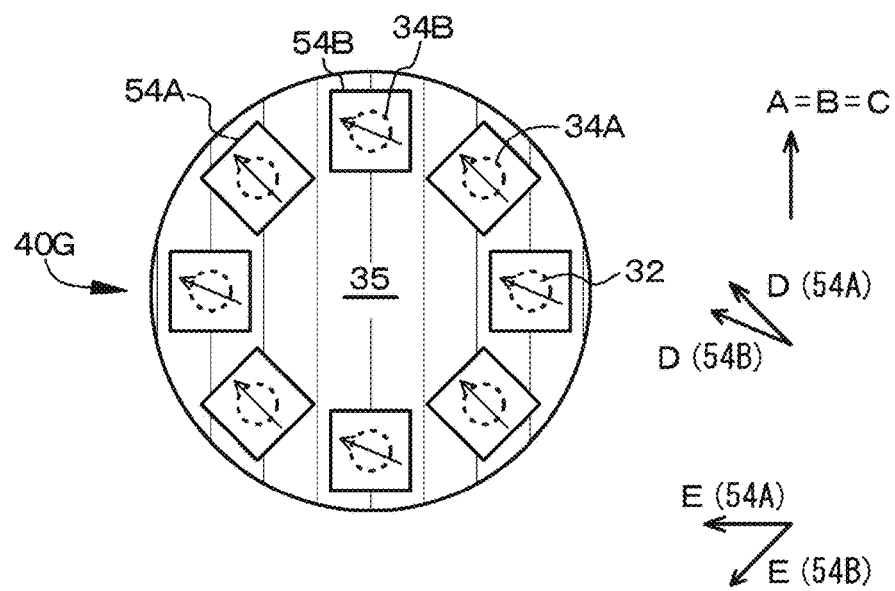

|  | FIG. 10A | FIG. 10A ½-WAVE PLATE | FIG. 10B | UNIT: DEGREE FIG. 10B |
|---|---|---|---|---|
|  | 54A | 54B | 54A | 54B |
| θ | 0 | 45 | 90 | 135 |
| φ | 0 | 22.5 | 45 | 67.5 |
| $\xi_{in}$ | 0 | 0 | 0 | 0 |
| $\xi_{out}$ | 0 | 45 | 90 | 135 |
| $\zeta_{in}$ | 0 | 0 | 0 | 0 |
| $\zeta_{out}$ | 0 | 45 | 90 | 135 |

Eighth Embodiment

Figure 11A:
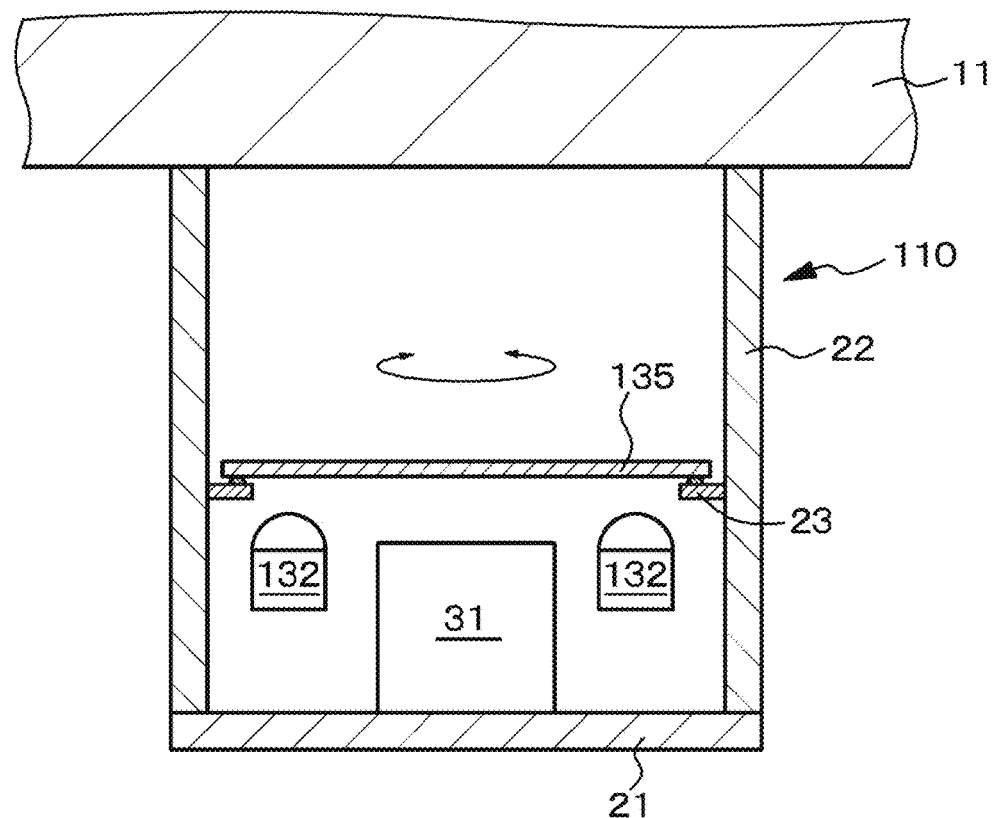
FIG. 11A and FIG. 11B are conceptual diagrams of an imaging device and a polarizer, respectively, according to an eighth embodiment.
Figure 11B:
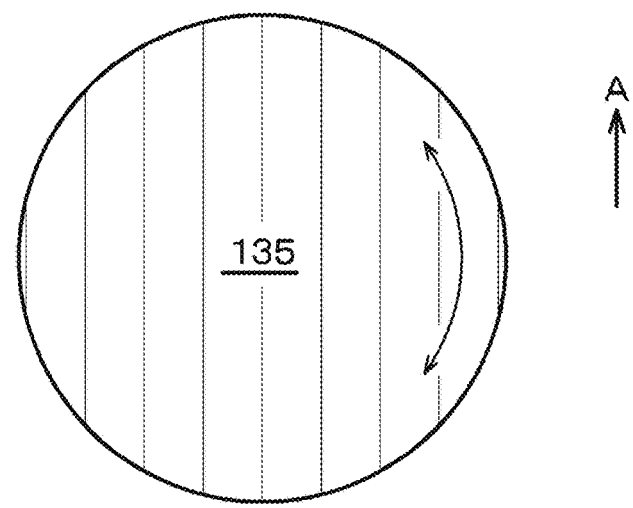

The eighth embodiment relates to the imaging device according to the second mode of the disclosure. A conceptual diagram of the imaging device according to the eighth embodiment is illustrated in FIG. 11A, whereas a conceptual diagram of a polarizer is illustrated in FIG. 11B. As illustrated therein, the imaging device according to the eighth embodiment includes a camera 31, a light source 132, and a polarizer 135 arranged between the camera 31 plus the light source 132 and an object 11, in which the polarizer 135 is arranged rotatably with respect to the camera 31 and the light source 132. In addition, the object 11 is imaged while the polarizer 135 is arranged at, for example, a position at zero degrees, a position at 45 degrees, a position at 90 degrees, and a position at 135 degrees with respect to the optimum arrangement angle $\zeta_0$ of the polarizer 135 relative to the camera 31 and the light source 133. Note that the imaging device according to the eighth embodiment has a configuration and a structure substantially similar to those of the imaging device according to the first embodiment except for not including the spatial light modulator 40A.

As described above, in the imaging device according to the eighth embodiment, the polarizer arranged rotatably with respect to the camera and the light source is provided between the camera plus the light source and the object. As a result, although the configuration and the structure thereof are simple, a polarization state of light from the object can be optimized in accordance with the object.

The imaging devices and the imaging methods according to the disclosure have been described thus far on the basis of the preferred embodiments. However, the imaging devices and the imaging methods according to the disclosure are not limited to these embodiments. The configurations and structures of the imaging devices and specific methods in the imaging methods described in the embodiments are merely examples and can be modified as appropriate. The embodiments have described exclusively an example where the epidermis (skin) is observed with the imaging devices according to the disclosure. However, the imaging devices and the imaging methods according to the disclosure can be used in another manner, for example, for the observation of a blood flow in a capillary vessel under scalp, which is enabled by suppressing reflection on a surface of the scalp.

Note that the disclosure can be also configured as described below.

[A01] <<Imaging Device: First Mode>>
An imaging device including:
a camera;
a light source;
a polarizer arranged between the camera plus the light source and an object; and
a spatial light modulator arranged between the polarizer and the object to control a revolution angle of an emitting light polarization plane relative to an incident light polarization plane.

[A02] The imaging device according to [A01], in which light emitting from the light source and passing through the polarizer and the spatial light modulator to collide with the object reaches the camera after passing through the polarizer.

[B01] <<Imaging Device: First A Mode>>
The imaging device according to [A01], in which the spatial light modulator is formed by a device provided with a transmission-type liquid crystal layer.

[B02] <<Imaging Device: First A-1 Mode>>
The imaging device according to [B01], in which light emitting from the light source and passing through the polarizer and the spatial light modulator to collide with the object reaches the camera after passing through the polarizer.

[B03] The imaging device according to [B02], in which the polarizer is arranged rotatably with respect to the camera and the light source, and
the spatial light modulator is fixed with respect to the polarizer.

[B04] The imaging device according to [B03], in which the revolution angle is changed to 0 degrees, 45 degrees, 90 degrees, and 135 degrees.

[B05] <<Imaging Device: First A-2 Mode>>
The imaging device according to [B01], in which
the spatial light modulator is constituted by an annular-shaped first region and a second region positioned on an inner side of the first region, and
light emitting from the light source and passing through the polarizer and the first region of the spatial light modulator to collide with the object reaches the camera after passing through the second region of the spatial light modulator and the polarizer.

[B06] The imaging device according to [B05], in which the polarizer and the spatial light modulator are fixed with respect to the camera and the light source.

[B07] The imaging device according to [B06], in which, when a value of an angle formed by the incident light polarization plane at the first region of the spatial light modulator and the emitting light polarization plane at the second region of the spatial light modulator is assumed as $\psi$ (in degree) and a value of an angle formed by the emitting light polarization plane at the first region of the spatial light modulator and the emitting light polarization plane at the second region of the spatial light modulator is assumed as $\psi'$ (in degree), the revolution angle at the first region of the spatial light modulator is changed by controlling operation of the first region of the spatial light modulator such that $\psi'$ is set to $\psi$ and a value different from $\psi$.

[B08] The imaging device according to [B07], in which $\psi'=\psi$, $\psi'=(\psi+45)$, $\psi'=(\psi+90)$, and $\psi'=(\psi+135)$ are set.

[B09] The imaging device according to [B08], in which $\psi=0$ is set.

[C01] <<Imaging Device: First B Mode>>
The imaging device according to [A01] or [A02], in which
the light source is constituted by a plurality of light emitting units arranged apart from one another,
the spatial light modulator is formed by a ½-wave plate that transmits light emitting from each of some of the plurality of light emitting units, and
a value of an angle $\phi$ formed by an optical axis of the ½-wave plate and the incident light polarization plane is not zero degrees.

[C02] <<Imaging Device: First B-1 Mode>>
The imaging device according to [C01], in which
the polarizer and the ½-wave plate are fixed with respect to the camera and the light source, and
the value of the angle $\phi$ is 45 degrees.

[C03] <<Imaging Device: First B-2 Mode>>
The imaging device according to [C01], in which
the polarizer is arranged rotatably with respect to the camera and the light source,
the ½-wave plate is fixed with respect to the polarizer, and
the value of the angle $\phi$ is 45 degrees.

[C04] The imaging device according to [C03], in which
the plurality of ½-wave plates is arranged in an annular shape, and
the polarizer is arranged at a position at zero degrees, a position at 45 degrees, a position at 90 degrees, and a position at 135 degrees with respect to an optimum arrangement angle of the polarizer relative to the camera and the light source.

[D01] <<Imaging Device: First C Mode>>
The imaging device according to [A01] or [A02], in which
the light source is constituted by a plurality of light emitting units arranged apart from one another,
the spatial light modulator is formed by M number of ½-wave plate groups, each of which is constituted by ½-wave plates that transmit light emitting from each of the plurality of light emitting units, and
when a value of an angle formed by the incident light polarization plane and an optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_1=0$ (in degree)

$|\phi_m-\phi_{m-1}|=\phi_0$ are satisfied.

[D02] <<Imaging Device: First C-1 Mode>>

The imaging device according to [D01], in which the polarizer and the ½-wave plate are fixed with respect to the camera and the light source.

[D03] The imaging device according to [D02], in which M=4 and $\phi_0$=22.5 degrees are set.

[D04] <<Imaging Device: First C-2 Mode>>

The imaging device according to [D01], in which the polarizer is arranged rotatably with respect to the camera and the light source, and the ½-wave plate is fixed with respect to the polarizer.

[D05] The imaging device according to [D04], in which the plurality of ½-wave plates is arranged in an annular shape, and the polarizer is arranged at a position at zero degrees and a position at 90 degrees with respect to an optimum arrangement angle of the polarizer relative to the camera and the light source.

[D06] The imaging device according to [D05], in which M=2 and $\phi_0$=22.5 degrees are set.

[D07] <<Imaging Device: First C-3 Mode>>

The imaging device according to [D01], in which the polarizer is arranged rotatably with respect to the camera and the light source, and the ½-wave plate is arranged rotatably with respect to the polarizer.

[D08] The imaging device according to [D07], in which the plurality of ½-wave plates is arranged in an annular shape, the polarizer is arranged so as to be fixed at zero degrees with respect to an optimum arrangement angle of the polarizer relative to the camera and the light source while the ½-wave plate is arranged at a position at zero degrees and a position at 45 degrees with respect thereto.

[D09] The imaging device according to [D08], in which M=2 and $\phi_0$=22.5 degrees are set.

[E01] <<Imaging Device: Second Mode>>

An imaging device including:

a camera;

a light source; and a polarizer arranged between the camera plus the light source and an object, in which the polarizer is arranged rotatably with respect to the camera and the light source.

[E02] The imaging device according to [E01], in which the polarizer is arranged at a position at zero degrees, a position at 45 degrees, a position at 90 degrees, and a position at 135 degrees with respect to an optimum arrangement angle of the polarizer relative to the camera and the light source.

[F01] <<Imaging Method: First Mode>>

An imaging method using an imaging device including:

a camera;

a light source;

a polarizer arranged between the camera plus the light source and an object; and a spatial light modulator arranged between the polarizer and the object to control a revolution angle of an emitting light polarization plane relative to an incident light polarization plane, in which the object is imaged with the camera while the revolution angle is changed.

[F02] <<Imaging Method: First A Mode>>

The imaging method according to [F01], in which the object is imaged with the camera while the polarizer and the spatial light modulator are rotated with respect to the camera and the light source in a state where the revolution angle is fixed and then, an optimum arrangement angle of the polarizer relative to the camera and the light source is determined such that an optimum reflection characteristic of the object is obtained, and subsequently, the object is imaged with the camera while the revolution angle is changed in a state where the polarizer and the spatial light modulator are fixed at the optimum arrangement angle.

[F03] The imaging method according to [F02], in which the spatial light modulator is formed by a device provided with a transmission-type liquid crystal layer.

[F04] The imaging method according to [F03], in which light emitting from the light source and passing through the polarizer and the spatial light modulator to collide with the object reaches the camera after passing through the polarizer.

[F05] The imaging method according to any one of [F02] to [F04], in which the object is imaged with the camera while the revolution angle is changed to zero degrees, 45 degrees, 90 degrees, and 135 degrees.

[G01] <<Imaging Method: First B Mode>>

The imaging method according to [F01], in which the object is imaged with the camera while the revolution angle is changed in a state where the polarizer and the spatial light modulator are fixed with respect to the camera and the light source and then, an optimum revolution angle relative to the camera and the light source is determined such that an optimum reflection characteristic of the object is obtained, and subsequently, the object is imaged with the camera while the revolution angle is set to the optimum revolution angle and a value different from the optimum revolution angle in a state where the polarizer and the spatial light modulator are fixed with respect to the camera and the light source.

[G02] The imaging method according to [G01], in which the spatial light modulator is constituted by an annular-shaped first region and a second region positioned on an inner side of the first region, and light emitting from the light source and passing through the polarizer and the first region of the spatial light modulator to collide with the object reaches the camera after passing through the second region of the spatial light modulator and the polarizer.

[G03] The imaging method according to [G02], in which, when a value of an angle formed by the incident light polarization plane at the first region of the spatial light modulator and the emitting light polarization plane at the second region of the spatial light modulator is assumed as $\psi$ (in degree) and a value of an angle formed by the emitting light polarization plane at the first region of the spatial light modulator and the emitting light polarization plane at the second region of the spatial light modulator is assumed as $\psi'$ (in degree), the object is imaged with the camera while the revolution angle at the first region of the spatial light modulator is changed by controlling operation of the first region of the spatial light modulator such that $\psi'$ is set to $\psi$ and a value different from $\psi$.

[G04] The imaging method according to [G03], in which $\psi'=\psi$, $\psi'=(\psi+45)$, $\psi'=(\psi+90)$, and $\psi'=(\psi+135)$ are set.

[G05] The imaging method according to [G04], in which ψ=0 is set.

[H01] <<Imaging Method: Second Mode>>
An imaging method using an imaging device including:
a camera;
a light source constituted by a plurality of light emitting units arranged apart from one another;
a polarizer arranged between the camera plus the light source and an object; and
a ½-wave plate arranged between the polarizer and the object to transmit light emitting from each of at least some of the plurality of light emitting units, in which
the object is imaged with the camera while the ½-wave plate and the polarizer are arranged such that a value of an angle φ formed by an optical axis of the ½-wave plate and a transmission axis of the polarizer is set to a value other than zero degrees.

[H02] The imaging method according to [H01], in which
the object is imaged with the camera while the polarizer and the ½-wave plate are rotated with respect to the camera and the light source and then, an optimum arrangement angle of the polarizer and the ½-wave plate relative to the camera and the light source is determined such that an optimum reflection characteristic of the object is obtained, and
subsequently, the object is imaged with the camera while the polarizer and the ½-wave plate are rotated by using the optimum arrangement angle as a reference.

[H03] The imaging method according to [H02], in which the value of the angle φ is 45 degrees.

[H04] The imaging method according to [H03], in which
the plurality of ½-wave plates is arranged in an annular shape, and
the object is imaged with the camera while the polarizer is arranged at a position at zero degrees, a position at 45 degrees, a position at 90 degrees, and a position at 135 degrees with respect to the optimum arrangement angle.

[J01] <<Imaging Method: Second B Mode>>
The imaging method according to [H01], in which
M number of ½-wave plate groups is provided, each of which is constituted by the plurality of ½-wave plates arranged apart from one another,
the polarizer is arranged rotatably with respect to the camera and the light source,
the ½-wave plate is fixed with respect to the polarizer,
when a value of an angle formed by an incident light polarization plane and the optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_1=0$ (in degree)

$|\phi_m-\phi_{m-1}|=\phi_0$ are satisfied, and
the object is imaged with the camera while the polarizer is rotated with respect to the camera and the light source and, after an optimum arrangement angle of the polarizer relative to the camera and the light source is determined such that an optimum reflection characteristic of the object is obtained, the object is imaged with the camera.

[J02] <<Imaging Method: Second B-1 Mode>>
The imaging method according to [J01], in which the object is imaged with the camera while the polarizer is arranged at the optimum arrangement angle.

[J03] The imaging method according to [J02], in which M=4 and $\phi_0$=22.5 degrees are set.

[J04] <<Imaging Method: Second B-2 Mode>>
The imaging method according to [J01], in which
the plurality of ½-wave plates is arranged in an annular shape, and
the object is imaged with the camera while the polarizer is arranged at a position at zero degrees and a position at 90 degrees with respect to the optimum arrangement angle.

[J05] The imaging method according to [J04], in which M=2 and $\phi_0$=22.5 degrees are set.

[K01] <<Imaging Method: Second C Mode>>
The imaging method according to [H01], in which
M number of ½-wave plate groups is provided, each of which is constituted by the plurality of ½-wave plates arranged apart from one another,
the polarizer is arranged rotatably with respect to the camera and the light source,
the entire ½-wave plates are arranged rotatably with respect to the polarizer,
when a value of an angle formed by an incident light polarization plane and the optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_1=0$ (in degree)

$|\phi_m-\phi_{m-1}|=\phi_0$ are satisfied,
the object is imaged with the camera while the polarizer and the entire ½-wave plates are rotated with respect to the camera and the light source and then, an optimum arrangement angle of the polarizer relative to the camera and the light source is determined such that an optimum reflection characteristic of the object is obtained, and
subsequently, the object is imaged with the camera while the entire ½-wave plates are rotated in a state where the polarizer is fixed at the optimum arrangement angle.

[K02] The imaging method according to [K01], in which
the entire ½-wave plates are arranged in an annular shape, and
the object is imaged with the camera while the entire ½-wave plates are arranged at a position at zero degrees and a position at 45 degrees with respect to the optimum arrangement angle.

[K03] The imaging method according to [K02], in which M=2 and $\phi_0$=22.5 degrees are set.

REFERENCE SIGNS LIST 10A, 10B, 10C, 10D, 10E, 10F, 10G Imaging device
11 Object
21 Pedestal
22 Light blocking member
23 Supporting unit
31 Camera
32, 33, 132 Light source
34A, 34B Light emitting unit
35 Polarizer 40A, 40B, 40C, 40D, 40E, 40F, 40G Spatial light modulator
41 First region of spatial light modulator
42 Second region of spatial light modulator
50A, 51A, 52A, 52B, 52C, 52D, 53A, 53B, 54A, 54B ½-wave plate

The invention claimed is:

1. An imaging device comprising:
   a camera;
   a light source;
   a polarizer arranged between the camera plus the light source and an object; and
   a spatial light modulator arranged between the polarizer and the object to control a revolution angle of an emitting light polarization plane relative to an incident light polarization plane, wherein
   the polarizer is arranged rotatably with respect to the camera and the light source, and
   the spatial light modulator is fixed with respect to the polarizer.

2. The imaging device according to claim 1, wherein the spatial light modulator is formed by a device provided with a transmission-type liquid crystal layer.

3. The imaging device according to claim 2, wherein light emitting from the light source and passing through the polarizer and the spatial light modulator to collide with the object reaches the camera after passing through the polarizer.

4. The imaging device according to claim 2, wherein
   the spatial light modulator is constituted by an annular-shaped first region and a second region positioned on an inner side of the first region, and
   light emitting from the light source and passing through the polarizer and the first region of the spatial light modulator to collide with the object reaches the camera after passing through the second region of the spatial light modulator and the polarizer.

5. The imaging device according to claim 1, wherein
   the light source is constituted by a plurality of light emitting units arranged apart from one another,
   the spatial light modulator is formed by a ½-wave plate that transmits light emitting from each of some of the plurality of light emitting units, and
   a value of an angle $\phi$ formed by an optical axis of the ½-wave plate and the incident light polarization plane is not zero degrees.

6. The imaging device according to claim 5, wherein
   the polarizer is arranged rotatably with respect to the camera and the light source,
   the ½-wave plate is fixed with respect to the polarizer, and
   the value of the angle $\phi$ is 45 degrees.

7. The imaging device according to claim 1, wherein
   the light source is constituted by a plurality of light emitting units arranged apart from one another,
   the spatial light modulator is formed by M number of ½-wave plate groups, each of which is constituted by ½-wave plates that transmit light emitting from each of the plurality of light emitting units, and
   when a value of an angle formed by the incident light polarization plane and an optical axis of the ½-wave plate in a first ½-wave plate group, which transmits light from a first light source group, is assumed as $\phi_1$ and a value of an angle formed by the incident light polarization plane and the optical axis of the ½-wave plate in an mth ½-wave plate group, which transmits light from an mth light source group (where m=2, 3, . . . , M), is assumed as $\phi_m$, $\phi_1 = 0$ (in degree)

$|\phi_m - \phi_{m-1}| = \phi_0$ are satisfied.

8. The imaging device according to claim 7, wherein
   the polarizer is arranged rotatably with respect to the camera and the light source, and
   the ½-wave plate is fixed with respect to the polarizer.

9. An imaging device comprising:
   a camera;
   a light source;
   a polarizer arranged between the camera plus the light source and an object; and
   a spatial light modulator arranged between the polarizer and the object, wherein
   the polarizer is arranged rotatably with respect to the camera and the light source.

10. An imaging method using an imaging device comprising:
    a camera;
    a light source;
    a polarizer arranged between the camera plus the light source and an object; and
    a spatial light modulator arranged between the polarizer and the object to control a revolution angle of an emitting light polarization plane relative to an incident light polarization plane, the method comprising:
    imaging the object with the camera while the revolution angle is changed, wherein
    the polarizer is arranged rotatably with respect to the camera and the light source, and
    the spatial light modulator is fixed with respect to the polarizer.

11. The imaging method according to claim 10, comprising:
    imaging the object with the camera while the polarizer and the spatial light modulator are rotated with respect to the camera and the light source in a state where the revolution angle is fixed and then, determining an optimum arrangement angle of the polarizer relative to the camera and the light source such that an optimum reflection characteristic of the object is obtained, and
    subsequently, imaging the object with the camera while the revolution angle is changed in a state where the polarizer and the spatial light modulator are fixed at the optimum arrangement angle.

12. The imaging method according to claim 10, comprising:
    imaging the object with the camera while the revolution angle is changed in a state where the polarizer and the spatial light modulator are fixed with respect to the camera and the light source and then, determining an optimum revolution angle relative to the camera and the light source such that an optimum reflection characteristic of the object is obtained, and
    subsequently, imaging the object with the camera while the revolution angle is set to the optimum revolution angle and a value different from the optimum revolution angle in a state where the polarizer and the spatial light modulator are fixed with respect to the camera and the light source.

13. An imaging method using an imaging device comprising:
- a camera;
- a light source constituted by a plurality of light emitting units arranged apart from one another;
- a polarizer arranged between the camera plus the light source and an object; and
- a ½-wave plate arranged between the polarizer and the object to transmit light emitting from each of at least some of the plurality of light emitting units, the method comprising:
- imaging the object with the camera while the ½-wave plate and the polarizer are arranged such that a value of an angle $\phi$ formed by an optical axis of the ½-wave plate and a transmission axis of the polarizer is set to a value other than zero degrees.

* * * * *